(12) United States Patent
Menn

(10) Patent No.: US 12,336,716 B2
(45) Date of Patent: Jun. 24, 2025

(54) SURGICAL CLIP APPLIER

(71) Applicant: Pavel Menn, Salem, MA (US)

(72) Inventor: Pavel Menn, Salem, MA (US)

(73) Assignee: MEGAFLEX SURGICAL CORPORATION, Islandia, NY (US)

( * ) Notice: Subject to any disclaimer, the term of this patent is extended or adjusted under 35 U.S.C. 154(b) by 0 days.

(21) Appl. No.: 18/231,206

(22) Filed: Aug. 7, 2023

(65) Prior Publication Data

US 2024/0041471 A1 Feb. 8, 2024

Related U.S. Application Data

(60) Provisional application No. 63/395,348, filed on Aug. 5, 2022.

(51) Int. Cl.
*A61B 17/128* (2006.01)
*A61B 17/122* (2006.01)
*A61B 17/00* (2006.01)

(52) U.S. Cl.
CPC ........ *A61B 17/1285* (2013.01); *A61B 17/122* (2013.01); *A61B 2017/0023* (2013.01)

(58) Field of Classification Search
CPC .............. A61B 17/1285; A61B 17/122; A61B 2017/0023; A61B 2017/00407; A61B 2017/0046
See application file for complete search history.

(56) References Cited

U.S. PATENT DOCUMENTS

| | | | |
|---|---|---|---|
| 7,717,926 B2 | 5/2010 | Whitfield et al. | |
| 7,819,886 B2 | 10/2010 | Whitfield et al. | |
| 8,262,679 B2 | 9/2012 | Nguyen | |
| 8,313,497 B2 | 11/2012 | Walberg et al. | |
| 8,409,222 B2 | 4/2013 | Whitfield et al. | |
| 2009/0228024 A1* | 9/2009 | Whitfield ........... | A61B 17/1285 606/143 |
| 2012/0029534 A1* | 2/2012 | Whitfield ........... | A61B 17/1285 606/143 |
| 2013/0190779 A1* | 7/2013 | Whitfield ........... | A61B 17/1285 606/143 |

* cited by examiner

*Primary Examiner* — Brooke Labranche
(74) *Attorney, Agent, or Firm* — Daniel N. Smith

(57) ABSTRACT

A surgical clip applier with a disposable surgical cartridge assembly and a non-disposable handle with a trigger for controlling the placement of surgical clips from the surgical cartridge assembly. The trigger moves an internal cinch to open surgical jaws to consecutively receive and hold surgical clips from a internal linear array of clips. Further movement of the trigger on handle moves the internal cinch to close the jaws and the surgical clip contained within over the ligation site.

11 Claims, 53 Drawing Sheets

SURGICAL CLIP APPLIER

CROSS REFERENCE TO RELATED APPLICATION

This application claims the benefit of, and priority to, U.S. Provisional Patent Application No. 63/395,348, filed Aug. 5, 2022, the contents of which are incorporated herein by reference.

FIELD OF THE INVENTION

This invention relates to a novel surgical clip applier for laparoscopic or endoscopic procedures.

BACKGROUND OF INVENTION

Laparoscopic and endoscopic surgical procedures are performed through small incisions in the skin or natural body orifices. Surgical clip appliers designed for these procedures are often separated into two components to reduce costs and minimize cross contamination.

The first component is a long and narrow surgical cartridge assembly that is inserted into the small opening during surgery. These surgical cartridge assemblies contain surgical clip appliers and a plurality of surgical clips. Surgical cartridge assemblies, since they are exposed to internal tissues and organs, are often one-use and disposable after the surgery is complete.

Surgeons employ surgical cartridge assemblies to ligate or occlude blood vessels in laparoscopic and endoscopic surgical procedures.

Control of the surgical cartridge assemblies is extremely important, as surgical clips must be securely and precisely fastened to blood vessels. Slippage or imprecise control of the surgical clip could damage the blood vessel, fail to close the blood vessel, damage nearby tissue, or interfere with the surgical site.

Precise and accurate control of small actuators on the first component is needed to control the movement and application of the surgical clips.

A second component is a non-disposable handle controlling the surgical cartridge assemblies. A surgeon may control the surgical cartridge assemblies by holding the handle and squeezing the trigger.

The subject invention is a new surgical clip applier with a disposable surgical cartridge assembly and a non-disposable handle with a trigger for controlling the placement of surgical clips from the surgical cartridge assembly.

SUMMARY OF THE INVENTION

There are additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses a surgical clip applier, comprising: a housing comprising a handle, and an opening on the housing; a drive mechanism movably disposed within the housing; a trigger attached to the housing, the trigger operably coupled to the drive mechanism, wherein application of compressive force to the trigger moves the trigger to from initial, first position, to at least two subsequent consecutive positions relative to the housing, wherein each trigger position moves the drive mechanism from a first initial configuration to at least two subsequent consecutive configurations; a cartridge assembly removably coupled to the housing, the cartridge assembly comprising a tubular housing, a coupling assembly adapted to removably couple the cartridge assembly to the housing; a pair of surgical jaws on the distal end of the cartridge assembly; a cinch rod disposed within the tubular housing, wherein the surgical jaws are operatively connected to the cinch rod; a linear array of sequentially centrally aligned surgical clips disposed within the tubular housing; a clip pusher disposed within the tubular housing; wherein compression of the trigger actuates the drive mechanism to move the cinch rod in a distal direction to open the surgical clip jaws to receive a distal most surgical clip from the linear array of surgical clips; wherein continued compression of the trigger actuates the drive mechanism to move the clip pusher in a distal direction to load the distal most surgical clip from the linear array of clips into the open surgical clip jaws; wherein continued compression of the trigger actuates the drive mechanism to move the cinch rod in a distal direction to begin closing the surgical clip jaws and compress the contained distal most surgical clip; and wherein continued compression of the actuates the drive mechanism from the third configuration to a fourth configuration to move the cinch rod in a distal direction to fully ligate the distal most surgical clip.

The subject invention also discloses an endoscopic surgical clip applier, comprising: a re-useable housing comprising a handle attached to a bottom surface of the housing, and an opening on a distal end of the housing; a drive mechanism movably disposed within the housing; a trigger attached to the bottom surface of the housing, the trigger operably coupled to the drive mechanism, wherein application of compressive force to the trigger moves the trigger in a proximal direction, wherein the trigger is configured to be moved from a first initial position to multiple consecutive positions relative to the housing, wherein each trigger position moves the drive mechanism from a first initial configuration to multiple separate consecutive configurations; an elongated cartridge assembly removably coupled to the housing and extending along a shaft axis from a proximal end to a distal end, the cartridge assembly comprising a hollow tubular housing, a coupling assembly disposed on the proximal end of the tubular housing and adapted to removably couple the proximal end of the cartridge assembly to the re-useable housing; a pair of surgical jaws on the distal end of the cartridge assembly; a cinch rod disposed within the tubular housing, wherein the surgical jaws are operatively connected to the cinch rod, wherein the cinch rod extends along the shaft axis; a substantially flat insert disposed beneath the cinch rod, within the tubular housing, wherein the flat insert extends along the shaft axis, wherein the flat insert further comprises a plurality of sequentially centrally aligned protrusions that extend in a downward direction; a linear array of sequentially centrally aligned surgical clips disposed within the tubular housing beneath the plurality of sequentially centrally aligned protrusions, wherein the linear array extends along the shaft axis; a substantially flat clip pusher disposed beneath the linear array of surgical clips within the tubular housing, wherein the clip pusher extends along the shaft axis, wherein the top surface of the clip pusher comprises a second plurality of protrusions disposed beneath the linear array of surgical clips; wherein compression of the trigger in a proximal direction from an initial position to a second position actuates the drive mechanism from a initial configuration to a second configuration to move the cinch rod in a distal direction to open the surgical clip jaws to receive a distal most surgical clip from the linear array of surgical clips; wherein continued compression of the trigger in a proximal direction from the second position to a third position actuates the drive mechanism from the second configuration to a third configuration to move the clip pusher in a distal direction to load the distal most surgical clip from the linear array of clips into the open surgical clip jaws; wherein continued compression of the trigger in a proximal direction from the third position to a fourth position actuates the drive mechanism from the third configuration to a fourth configuration to move the cinch rod in a distal direction to begin closing the surgical clip jaws and compress the contained distal most surgical clip; and wherein continued compression of the trigger in a proximal direction from the fourth position to a fifth position actuates the drive mechanism from the third configuration to a fourth configuration to move the cinch rod in a distal direction to fully ligate the distal most surgical clip.

The subject invention further discloses an endoscopic surgical clip applier, comprising: a re-useable housing comprising a handle, and an opening on a distal end of the housing; a drive mechanism movably disposed within the housing; a trigger attached to the housing, the trigger operably coupled to the drive mechanism, wherein application of compressive force to the trigger moves the trigger in a proximal direction from a first initial position to subsequent consecutive positions relative to the housing, wherein each trigger position moves the drive mechanism from a first initial configuration to subsequent configurations; a cartridge assembly removably coupled to the housing and extending along a shaft axis from a proximal end to a distal end, the cartridge assembly comprising a hollow tubular housing, a coupling assembly disposed on the proximal end of the tubular housing and adapted to removably couple the proximal end of the cartridge assembly to the re-useable housing; a pair of surgical jaws on the distal end of the cartridge assembly; a cinch rod disposed within the tubular housing, wherein the surgical jaws are operatively connected to the cinch rod, wherein the cinch rod extends along the shaft axis; an insert disposed beneath the cinch rod, within the tubular housing, wherein the insert extends along the shaft axis, wherein the flat insert further comprises a plurality of sequentially centrally aligned protrusions that extend in a downward direction; a linear array of sequentially centrally aligned surgical clips disposed within the tubular housing beneath the plurality of sequentially centrally aligned protrusions, wherein the linear array extends along the shaft axis; a clip pusher disposed beneath the linear array of surgical clips within the tubular housing, wherein the clip pusher extends along the shaft axis, wherein the top surface of the clip pusher comprises a second plurality of protrusions disposed beneath the linear array of surgical clips; wherein compression of the trigger in a proximal direction from an initial position to a second position actuates the drive mechanism from a initial configuration to a second configuration to move the cinch rod in a distal direction to open the surgical clip jaws to receive a distal most surgical clip from the linear array of surgical clips; wherein continued compression of the trigger in a proximal direction from the second position to a third position actuates the drive mechanism from the second configuration to a third configuration to move the clip pusher in a distal direction to load the distal most surgical clip from the linear array of clips into the open surgical clip jaws; wherein continued compression of the trigger in a proximal direction from the third position to a fourth position actuates the drive mechanism from the third configuration to a fourth configuration to move the cinch rod in a distal direction to begin closing the surgical clip jaws and compress the contained distal most surgical clip; and wherein continued compression of the trigger in a proximal direction from the fourth position to a fifth position actuates the drive mechanism from the third configuration to a fourth configuration to move the cinch rod in a distal direction to fully ligate the distal most surgical clip.

The subject invention discloses a surgical clip applier, comprising: a housing comprising a handle, and an opening on the housing; a drive mechanism movably disposed within the housing; a trigger attached to the housing, the trigger operably coupled to the drive mechanism, wherein application of compressive force to the trigger moves the trigger to from initial, first position, to at least two subsequent consecutive positions relative to the housing, wherein each trigger position moves the drive mechanism from a first initial configuration to at least two subsequent consecutive configurations; a cartridge assembly removably coupled to the housing, the cartridge assembly comprising a tubular housing, a coupling assembly adapted to removably couple the cartridge assembly to the housing; a pair of surgical jaws on the distal end of the cartridge assembly, wherein each surgical jaw contains a protruding pin; a cinch rod disposed within the tubular housing, wherein the pins of the surgical jaws are contained within an indentation of the cinch rod; a linear array of sequentially centrally aligned surgical clips disposed within the tubular housing; a clip pusher disposed within the tubular housing; wherein compression of the trigger actuates the drive mechanism to move the cinch rod in a distal direction, moving the indentation of the cinch rod over the pins of the surgical jaws to a wider portion of the indentation, widening the space between the surgical clip jaws to receive a distal most surgical clip from the linear array of surgical clips; wherein continued compression of the trigger actuates the drive mechanism to move the clip pusher in a distal direction to load the distal most surgical clip from the linear array of clips into the open surgical clip jaws; wherein continued compression of the trigger actuates the drive mechanism to move the cinch rod in a distal direction, moving the indentation of the cinch rod over the pins of the surgical jaws to a first narrow portion of the indentation, narrowing the space between the surgical clip jaws to begin closing the surgical clip jaws and compress the contained distal most surgical clip; and wherein continued compression of the actuates the drive mechanism from the third configuration to a fourth configuration to move the cinch rod in a distal direction, moving the indentation of the cinch rod over the pins of the surgical jaws to a second narrow portion of the indentation, narrowing the space between the surgical clip jaws to fully ligate the distal most surgical clip.

The subject invention discloses a surgical clip applier, comprising: a housing comprising a handle, and an opening on the housing; a drive mechanism movably disposed within the housing; a trigger attached to the housing, the trigger operably coupled to the drive mechanism, wherein application of compressive force to the trigger moves the trigger to from initial, first position, to at least two subsequent consecutive positions relative to the housing, wherein each trigger position moves the drive mechanism from a first initial configuration to at least two subsequent consecutive configurations; a cartridge assembly removably coupled to the housing, the cartridge assembly comprising a tubular housing, a coupling assembly adapted to removably couple the cartridge assembly to the housing; a pair of surgical jaws on the distal end of the cartridge assembly, wherein each surgical jaw contains at least one protrusion; a cinch rod disposed within the tubular housing, wherein the protrusions of the surgical jaws are contained within an indentation of the cinch rod; a linear array of sequentially centrally aligned surgical clips disposed within the tubular housing; a clip pusher disposed within the tubular housing; wherein compression of the trigger actuates the drive mechanism to move the cinch rod in a distal direction, moving the indentation of the cinch rod over the protrusions of the surgical jaws to a wider portion of the indentation, widening the space between the surgical clip jaws to receive a distal most surgical clip from the linear array of surgical clips; wherein continued compression of the trigger actuates the drive mechanism to move the clip pusher in a distal direction to load the distal most surgical clip from the linear array of clips into the open surgical clip jaws; wherein continued compression of the trigger actuates the drive mechanism to move the cinch rod in a distal direction, moving the indentation of the cinch rod over the protrusions of the surgical jaws to a first narrow portion of the indentation, narrowing the space between the surgical clip jaws to begin closing the surgical clip jaws and compress the contained distal most surgical clip; and wherein continued compression of the actuates the drive mechanism from the third configuration to a fourth configuration to move the cinch rod in a distal direction, moving the indentation of the cinch rod over the protrusions of the surgical jaws to a second narrow portion of the indentation, narrowing the space between the surgical clip jaws to fully ligate the distal most surgical clip.

The subject invention discloses a surgical clip applier, comprising: a housing comprising a handle, and an opening on the housing; a drive mechanism movably disposed within the housing; a trigger attached to the housing, the trigger operably coupled to the drive mechanism, wherein application of compressive force to the trigger moves the trigger to from initial, first position, to at least two subsequent consecutive positions relative to the housing, wherein each trigger position moves the drive mechanism from a first initial configuration to at least two subsequent consecutive configurations; a cartridge assembly removably coupled to the housing, the cartridge assembly comprising a tubular housing, a coupling assembly adapted to removably couple the cartridge assembly to the housing; a pair of surgical jaws on the distal end of the cartridge assembly, wherein each surgical jaw contains at least one protruding pin; a cinch rod disposed within the tubular housing, wherein the pins of the surgical jaws are contained within a pin guide on the cinch rod; a linear array of sequentially centrally aligned surgical clips disposed within the tubular housing; a clip pusher disposed within the tubular housing; wherein compression of the trigger actuates the drive mechanism to move the cinch rod in a distal direction, moving the pin guide of the cinch rod over the pins of the surgical jaws to a wider portion of the pin guide, widening the space between the surgical clip jaws to receive a distal most surgical clip from the linear array of surgical clips; wherein continued compression of the trigger actuates the drive mechanism to move the clip pusher in a distal direction to load the distal most surgical clip from the linear array of clips into the open surgical clip jaws; wherein continued compression of the trigger actuates the drive mechanism to move the cinch rod in a distal direction, moving the pin guide of the cinch rod over the pins of the surgical jaws to a first narrow portion of the pin guide, narrowing the space between the surgical clip jaws to begin closing the surgical clip jaws and compress the contained distal most surgical clip; and wherein continued compression of the actuates the drive mechanism from the third configuration to a fourth configuration to move the cinch rod in a distal direction, moving the pin guide of the cinch rod over the pins of the surgical jaws to a second narrow portion of the pin guide, narrowing the space between the surgical clip jaws to fully ligate the distal most surgical clip.

The subject invention discloses a surgical clip applier, comprising: a housing comprising a handle, and an opening on the housing; a drive mechanism movably disposed within the housing; a trigger attached to the housing, the trigger operably coupled to the drive mechanism, wherein application of compressive force to the trigger moves the trigger to from initial, first position, to at least two subsequent consecutive positions relative to the housing, wherein each trigger position moves the drive mechanism from a first initial configuration to at least two subsequent consecutive configurations; a cartridge assembly removably coupled to the housing, the cartridge assembly comprising a tubular housing, a coupling assembly adapted to removably couple the cartridge assembly to the housing; a pair of surgical jaws on the distal end of the cartridge assembly, wherein each surgical jaw contains at least one protruding pin; a cinch rod disposed within the tubular housing, wherein the pins of the surgical jaws are contained within a pin guide on the cinch rod; a linear array of sequentially centrally aligned surgical clips disposed within the tubular housing; a clip pusher disposed within the tubular housing; wherein compression of the trigger actuates the drive mechanism to move the cinch rod and pin guide in a distal direction, moving the pins of the surgical jaws to control the space between the surgical clip jaws to receive a distal most surgical clip from the linear array of surgical clips and close surgical clip jaws to fully ligate the distal most surgical clip.

The subject invention discloses a surgical clip applier, comprising: a housing comprising a handle, and an opening on the housing; a drive mechanism movably disposed within the housing; a trigger attached to the housing, the trigger operably coupled to the drive mechanism, wherein application of compressive force to the trigger moves the trigger to from initial, first position, to at least two subsequent consecutive positions relative to the housing, wherein each trigger position moves the drive mechanism from a first initial configuration to at least two subsequent consecutive configurations; a cartridge assembly removably coupled to the housing, the cartridge assembly comprising a tubular housing, a coupling assembly adapted to removably couple the cartridge assembly to the housing; a pair of surgical jaws on the distal end of the cartridge assembly, wherein each surgical jaw contains at least one protruding pin; a cinch rod disposed within the tubular housing, wherein the pins of the surgical jaws are contained within a pin guide on the cinch rod; a linear array of sequentially centrally aligned surgical clips disposed within the tubular housing; a clip pusher disposed within the tubular housing; wherein compression of the trigger actuates the drive mechanism to move the cinch rod and pin guide in a distal direction, moving the pins of the surgical jaws to a wider position within the pin guide, widening the space between the surgical clip jaws to receive a distal most surgical clip from the linear array of surgical clips; wherein continued compression of the trigger actuates the drive mechanism to move the clip pusher in a distal direction to load the distal most surgical clip from the linear array of clips into the open surgical clip jaws; wherein continued compression of the trigger actuates the drive mechanism to move the cinch rod and pin guide in a distal direction, moving the pins of the surgical jaws to a narrower position within the pin guide, narrowing the space between the surgical clip jaws to begin closing the surgical clip jaws and compress the contained distal most surgical clip; and wherein continued compression of the actuates the drive mechanism from the third configuration to a fourth configuration to move the cinch rod and the pin guide in a distal direction, moving the pins of the surgical jaws to a second narrow position within the pin guide, narrowing the space between the surgical clip jaws to fully ligate the distal most surgical clip.

In further embodiments of the subject invention, the cartridge assembly may be disposable.

In other embodiments of the subject invention, the housing assembly may be re-useable.

In embodiments of the subject invention, the housing, the drive mechanism, the trigger, the cartridge assembly, the cinch rod, and the linear array of surgical clips, and the clip pusher may operate at any angle.

In further embodiments of the subject invention, the cartridge assembly is one of a 5 millimeter surgical clip cartridge or a 10 millimeter surgical clip cartridge.

In other embodiments of the subject invention, each surgical clip comprises a pair of opposed elongated ligating legs that have substantially uniform widths and lengths.

In additional embodiments of the subject invention, the trigger is configured to be moved from a first initial position to a second, a third, a fourth, a fifth, and a sixth position relative to the housing to move the drive mechanism from a first initial configuration to a second, a third, a fourth, a fifth, and a sixth configuration.

In further embodiments of the subject invention, the surgical clip jaws compress the contained distal most surgical clip by applying two substantially equal compressive forces in opposing directions to the outer surface of ligating legs towards the center of the surgical clip, such that the ligating legs bend at an apex connection until a vessel diameter is reduced to a desired level.

Other embodiments of the subject invention may further comprise a locking mechanism disposed within the housing, wherein the locking mechanism prevents proximal movement of the cinch rod, the clip pusher, and the linear array of surgical clips without movement of the trigger.

Additional embodiments of the subject invention may further comprise a locking mechanism disposed within the housing, wherein the locking mechanism temporarily maintains the position of the cinch rod, the clip pusher, and the linear array of surgical clips at each position of the trigger.

In embodiments of the subject invention, the term "substantially" is defined as at least close to (and can include) a given value or state, as understood by a person of ordinary skill in the art. In one embodiment, the term "substantially" refers to ranges within 10%, preferably within 5%, more preferably within 1%, and most preferably within of the given value or state being specified.

In embodiments of the subject invention, the term "relatively" is defined as a comparison of a property, or the proportion of a property between two components.

BRIEF DESCRIPTION OF THE DRAWINGS

Advantages of the present invention will be apparent from the following detailed description of embodiments, which description should be considered in conjunction with the accompanying drawings, in which.

DETAILED DESCRIPTION OF THE EMBODIMENTS

Figure 1:
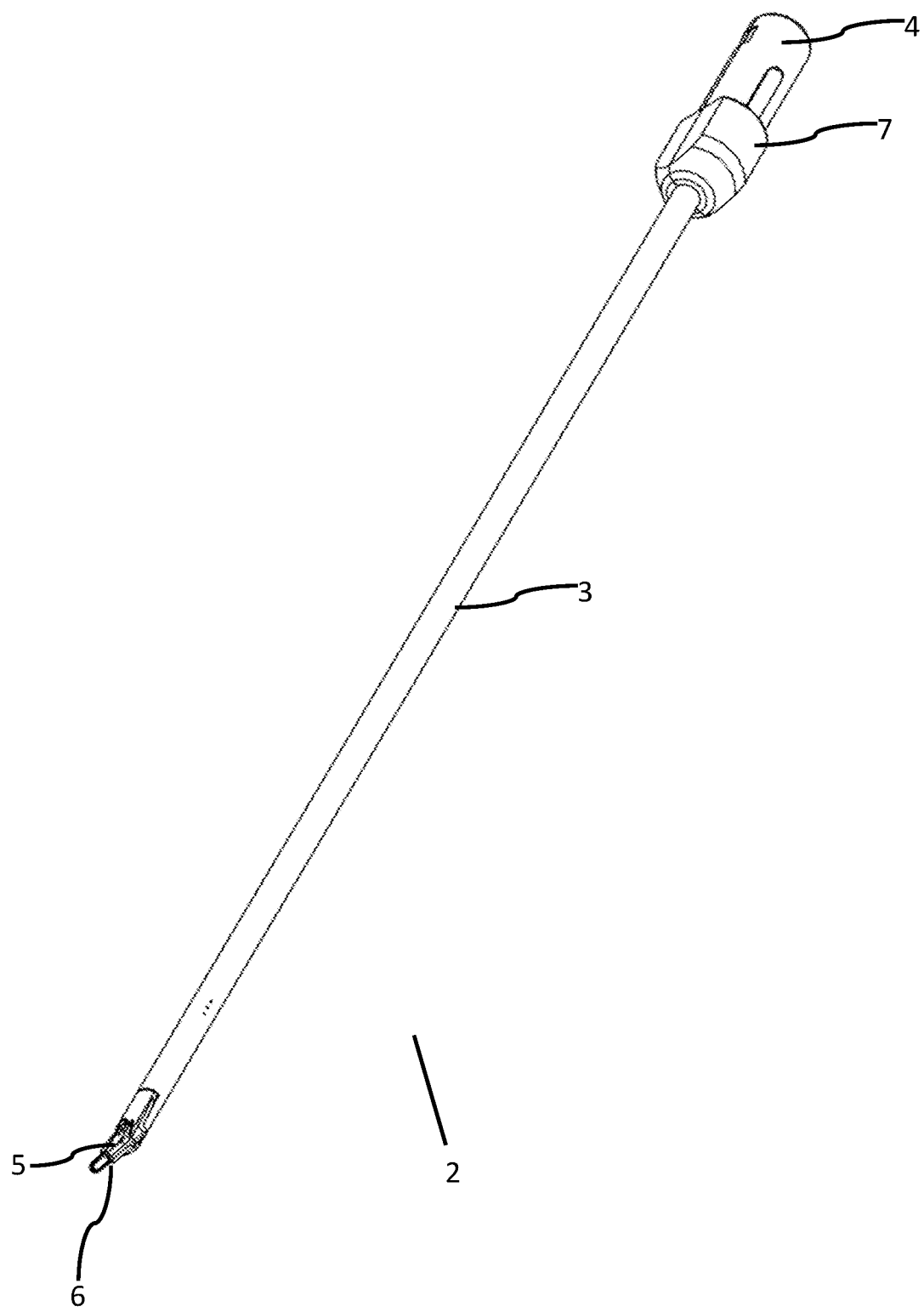
FIG. 1 Illustrates a perspective view of a surgical clip cartridge assembly for use with a surgical clip applier handle.
Figure 2:
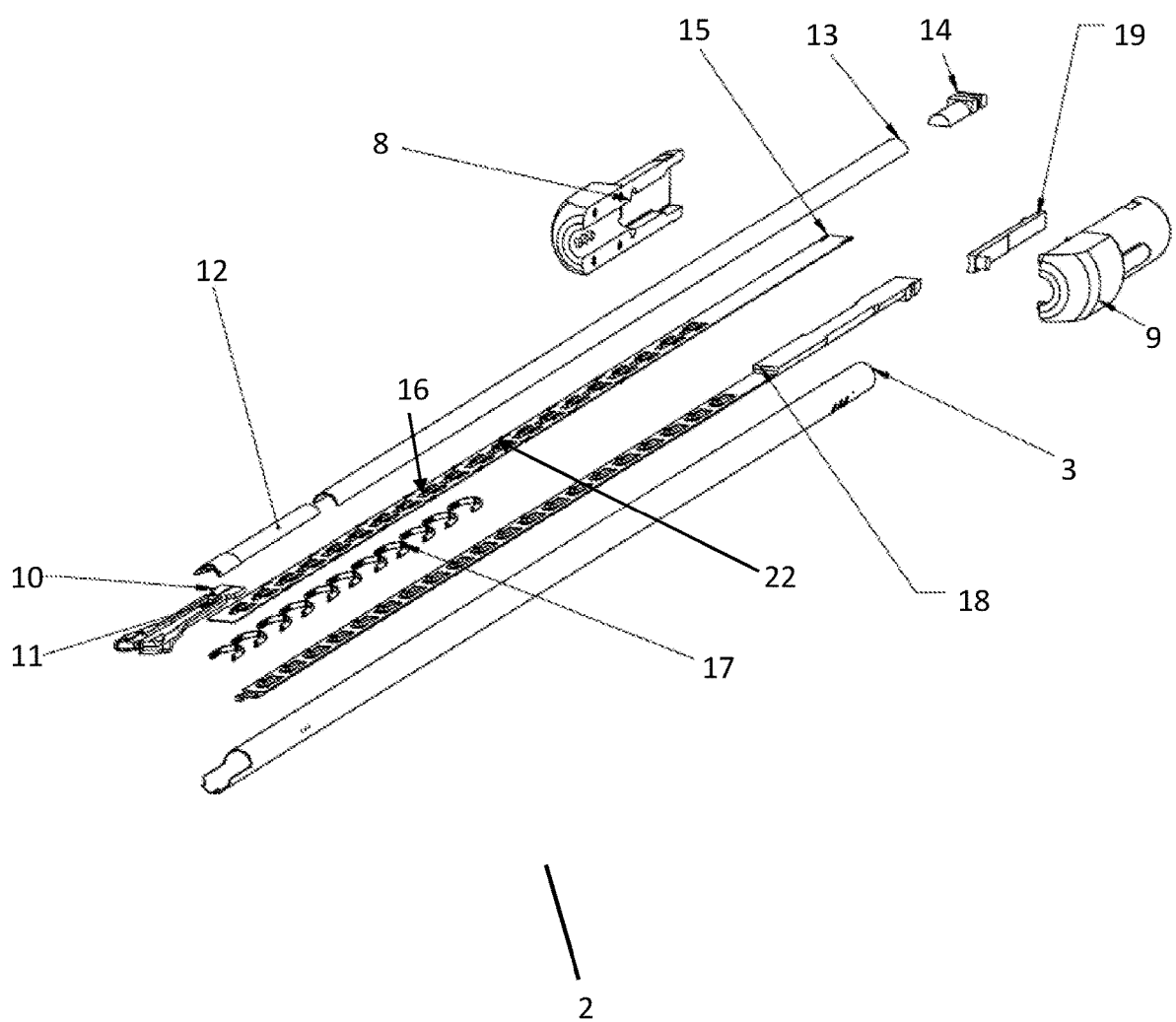
FIG. 2 Illustrates an exploded perspective view of the surgical clip cartridge assembly for use with the surgical clip applier handle.
Figure 3:
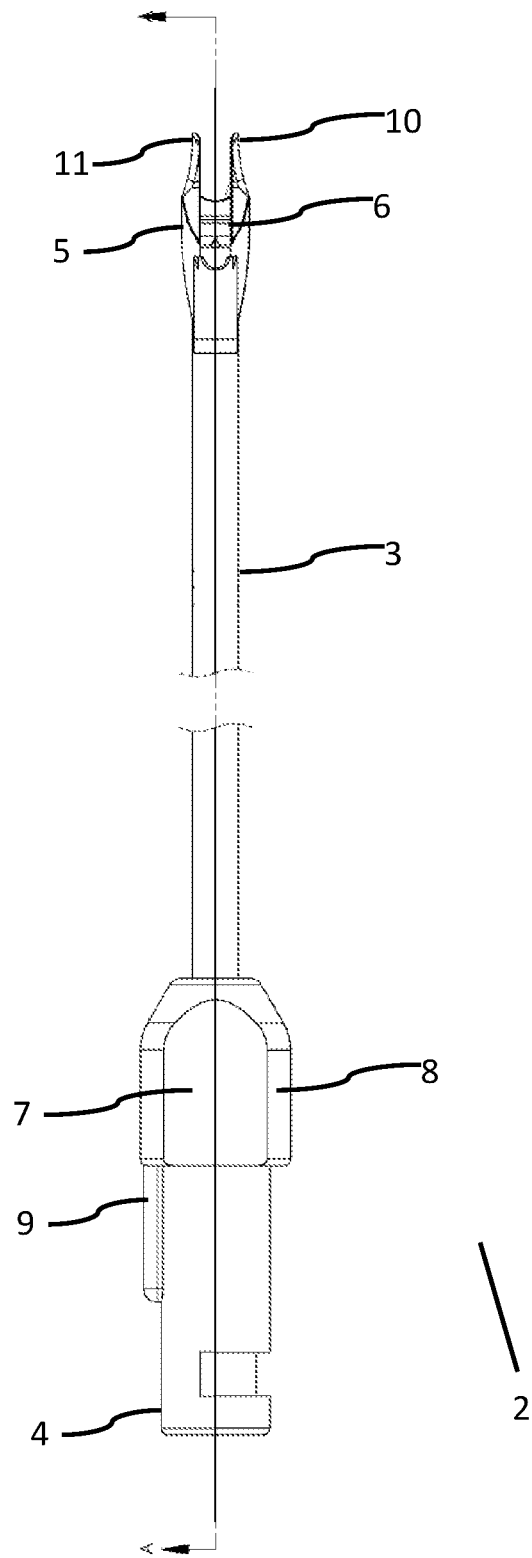
FIG. 3 Illustrates a top view of the surgical clip cartridge assembly in the initial cartridge position.
Figure 4:
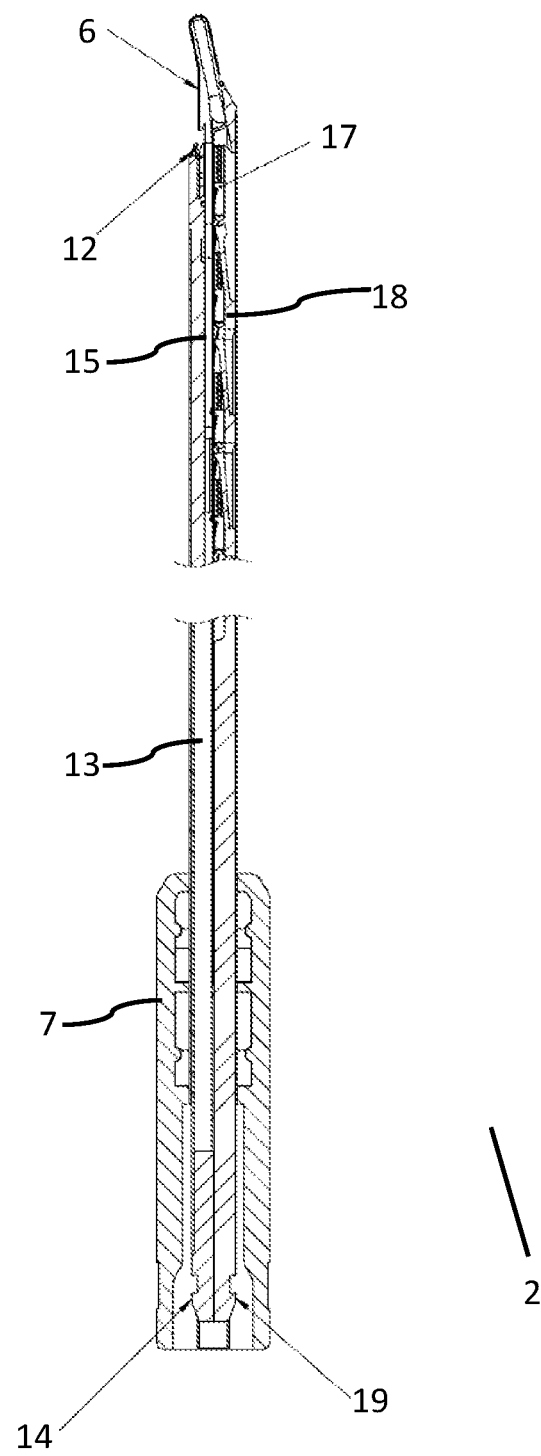
FIG. 4 Illustrates a side cross-sectional view of the surgical clip cartridge assembly in the initial cartridge position along line A-A in FIG. 3.
Figure 5:
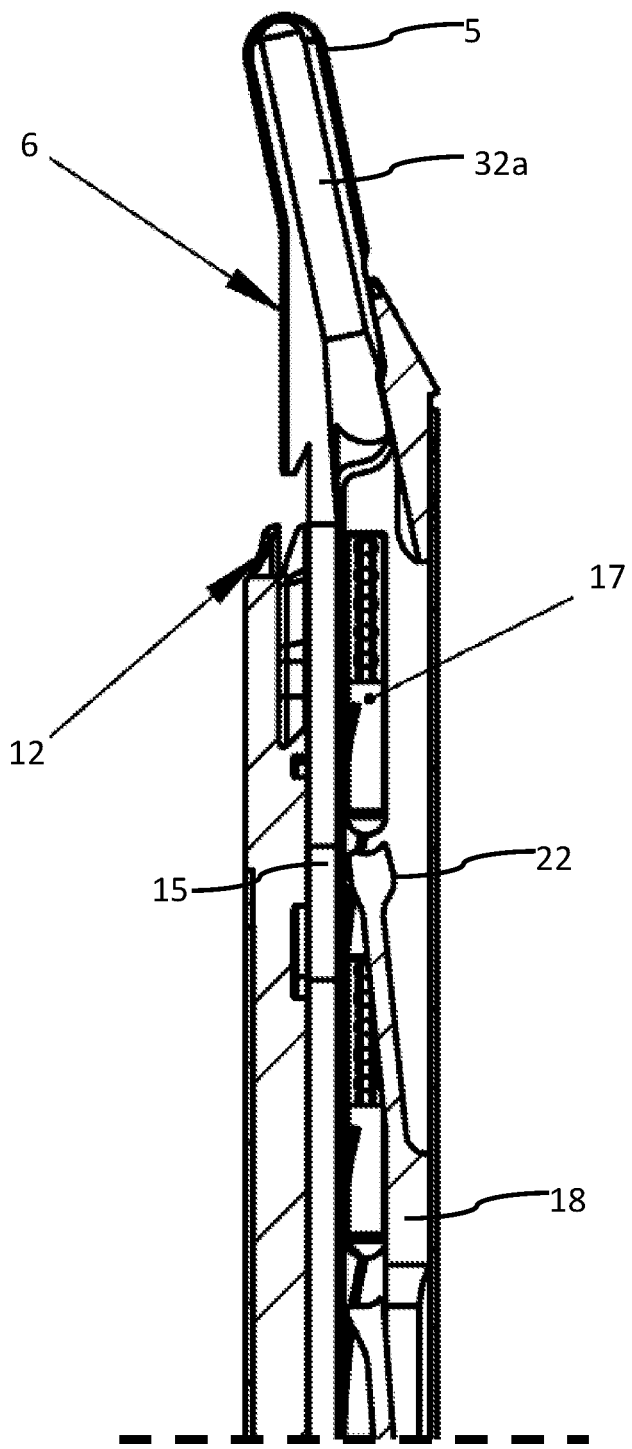
FIG. 5 Illustrates an exploded cross-sectional view of the distal end of the surgical clip cartridge assembly from FIG. 4.
Figure 6:
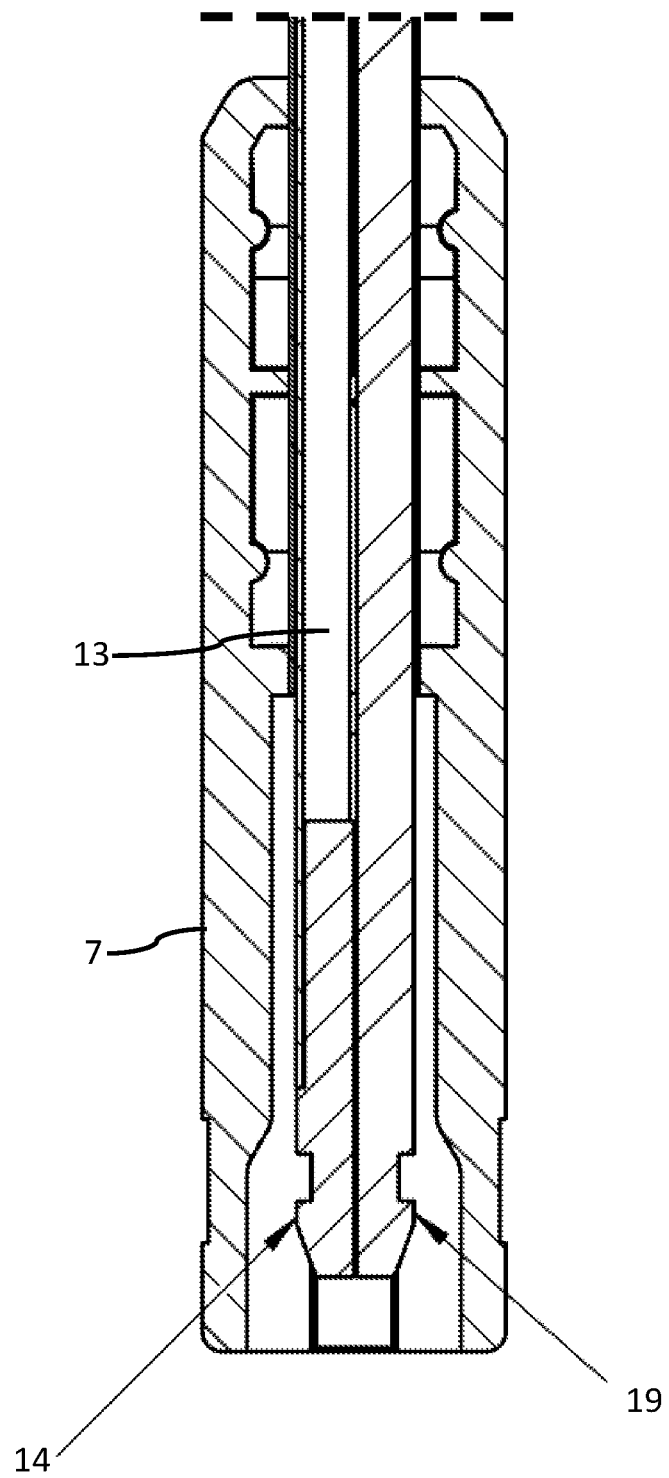
FIG. 6 Illustrates an exploded cross-sectional view of the proximal end of the surgical clip cartridge assembly from FIG. 4.
Figure 7:
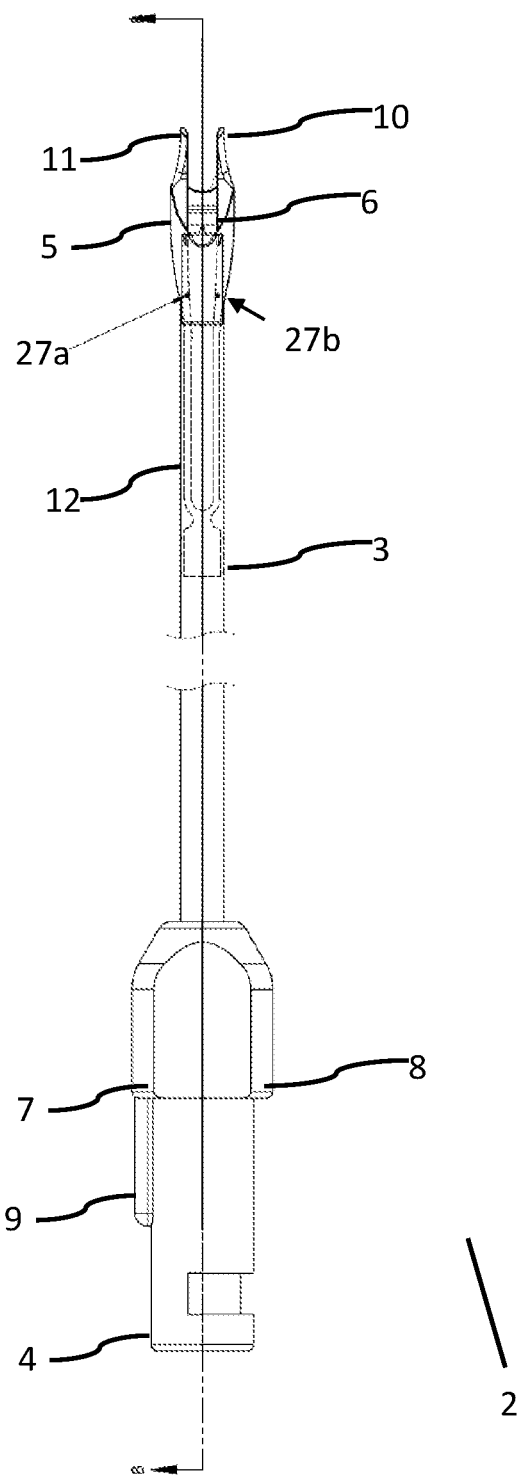
FIG. 7 Illustrates a top view of the surgical clip cartridge assembly in the second cartridge position.
Figure 8:
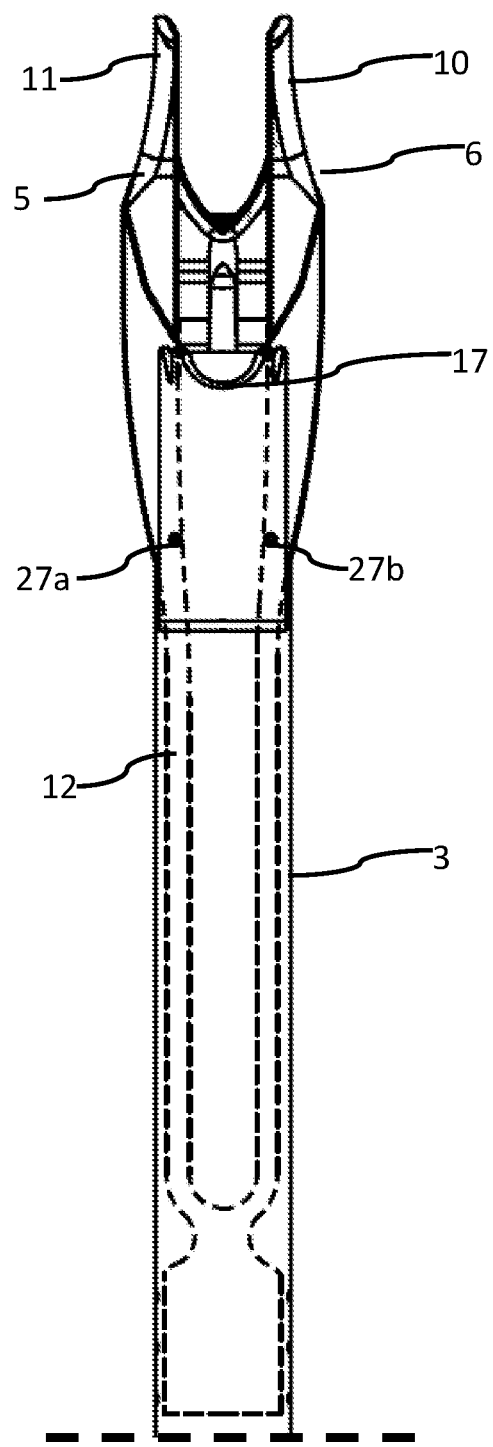
FIG. 8 Illustrates an exploded top view of the distal end of the surgical clip cartridge assembly in the second cartridge position from FIG. 7.
Figure 9:
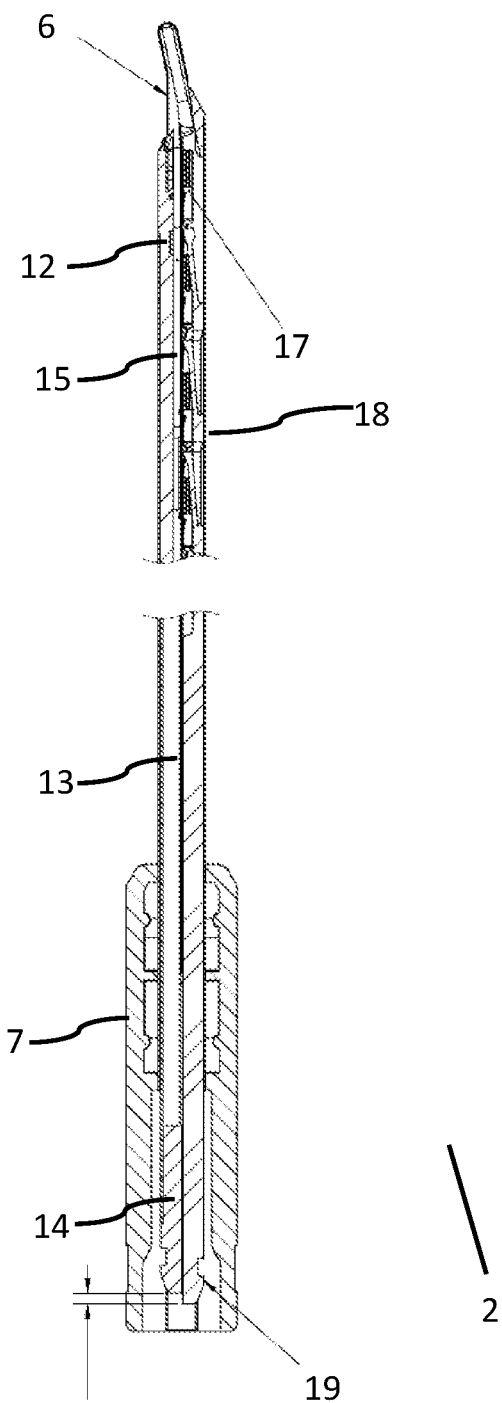
FIG. 9 Illustrates a side cross-sectional view of the surgical clip cartridge assembly in the second cartridge position along line B-B in FIG. 7.
Figure 10:
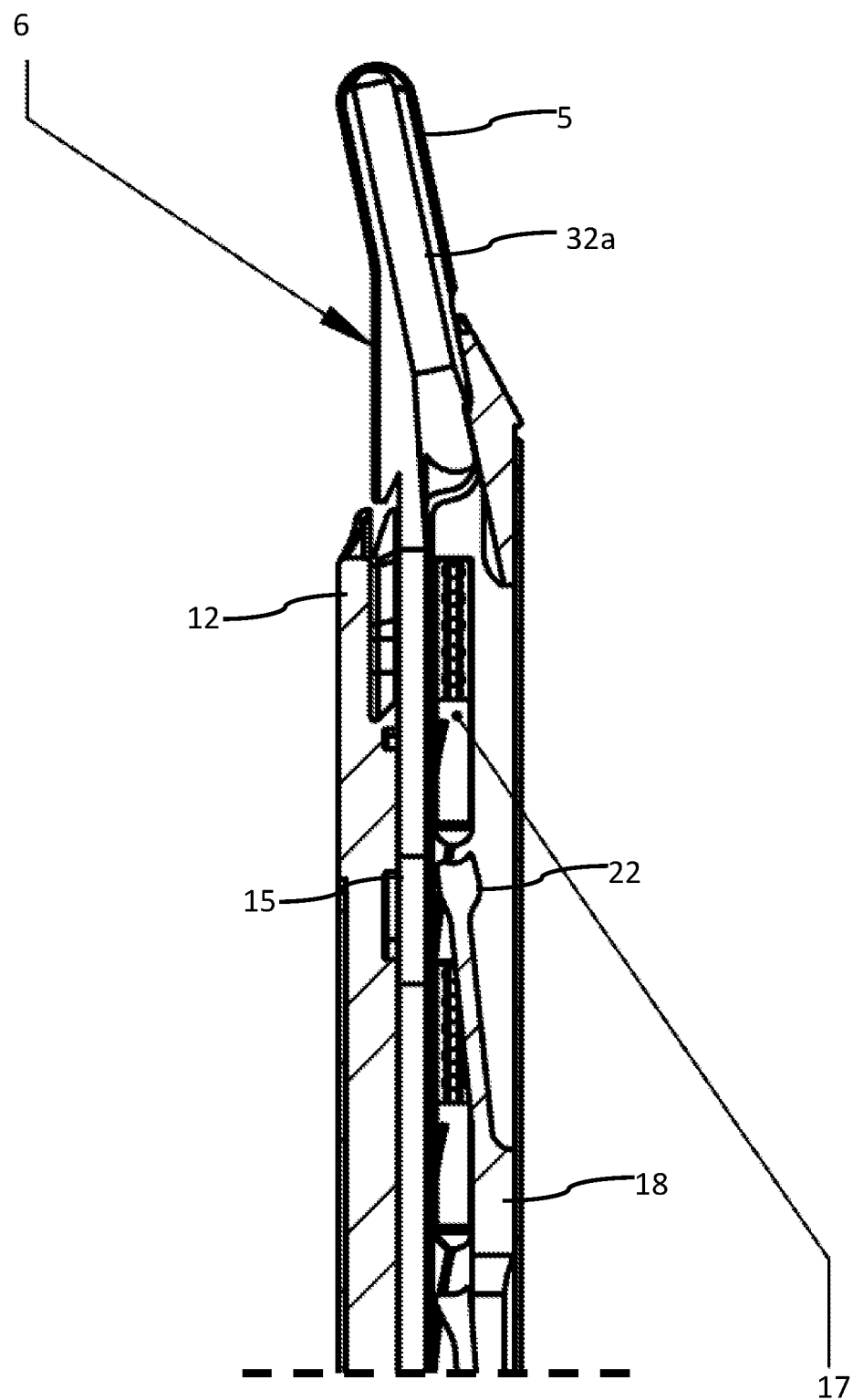
FIG. 10 Illustrates an exploded cross-sectional view of the distal end of the surgical clip cartridge assembly from FIG. 9.
Figure 11:
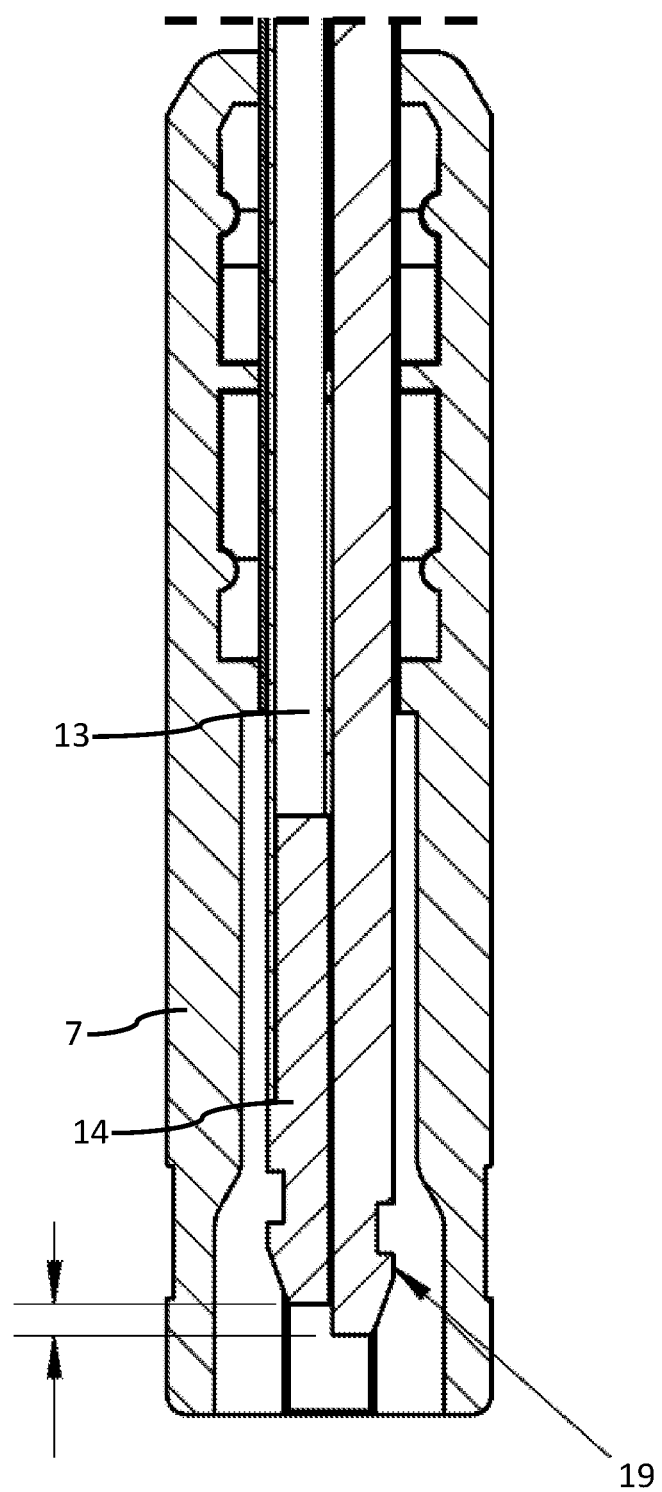
FIG. 11 Illustrates an exploded cross-sectional view of the proximal end of the surgical clip cartridge assembly from FIG. 9.
Figure 12:
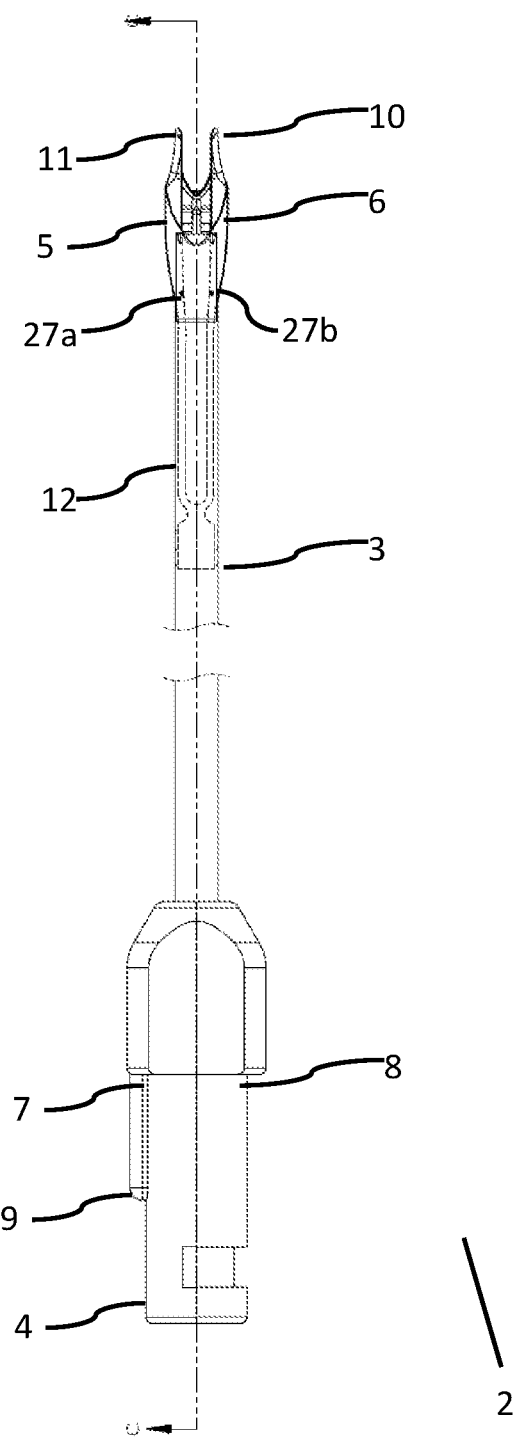
FIG. 12 Illustrates a top view of the surgical clip cartridge assembly in the third cartridge position.
Figure 13:
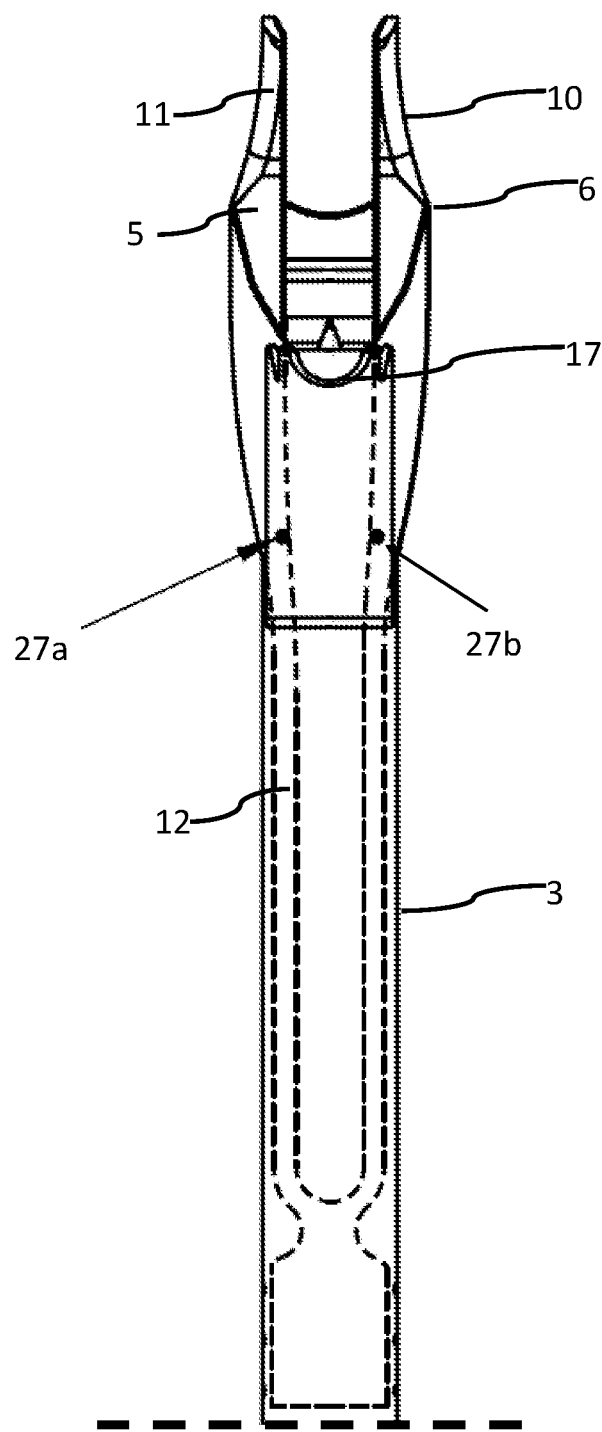
FIG. 13 Illustrates an exploded top view of the distal end of the surgical clip cartridge assembly in the third cartridge position from FIG. 12
Figure 14:
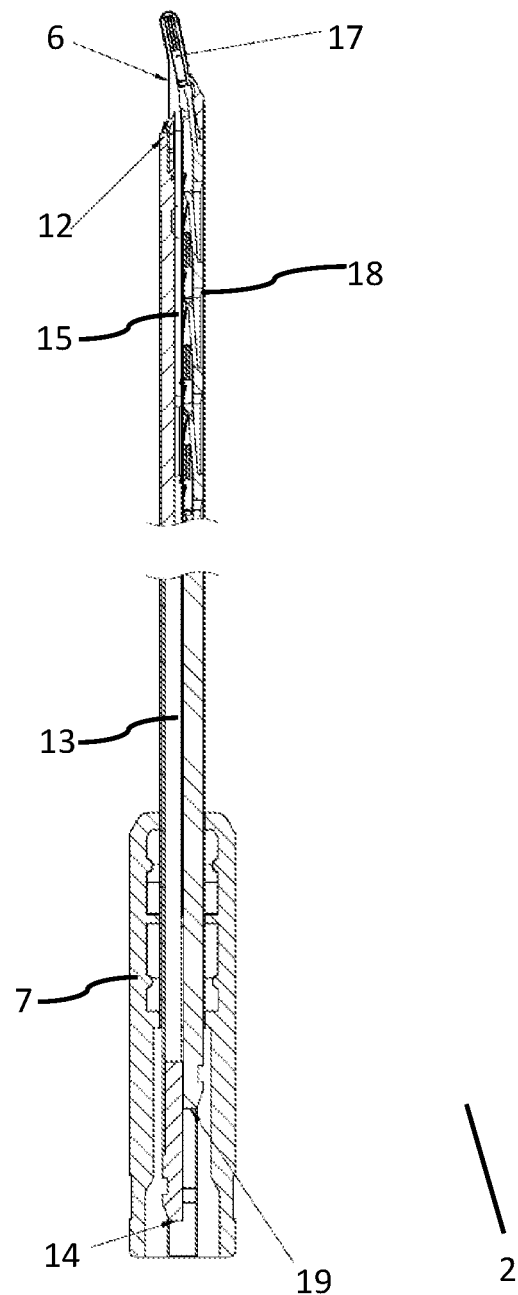
FIG. 14 Illustrates a side cross-sectional view of the surgical clip cartridge assembly in the third cartridge position along line C-C in FIG. 12.
Figure 15:
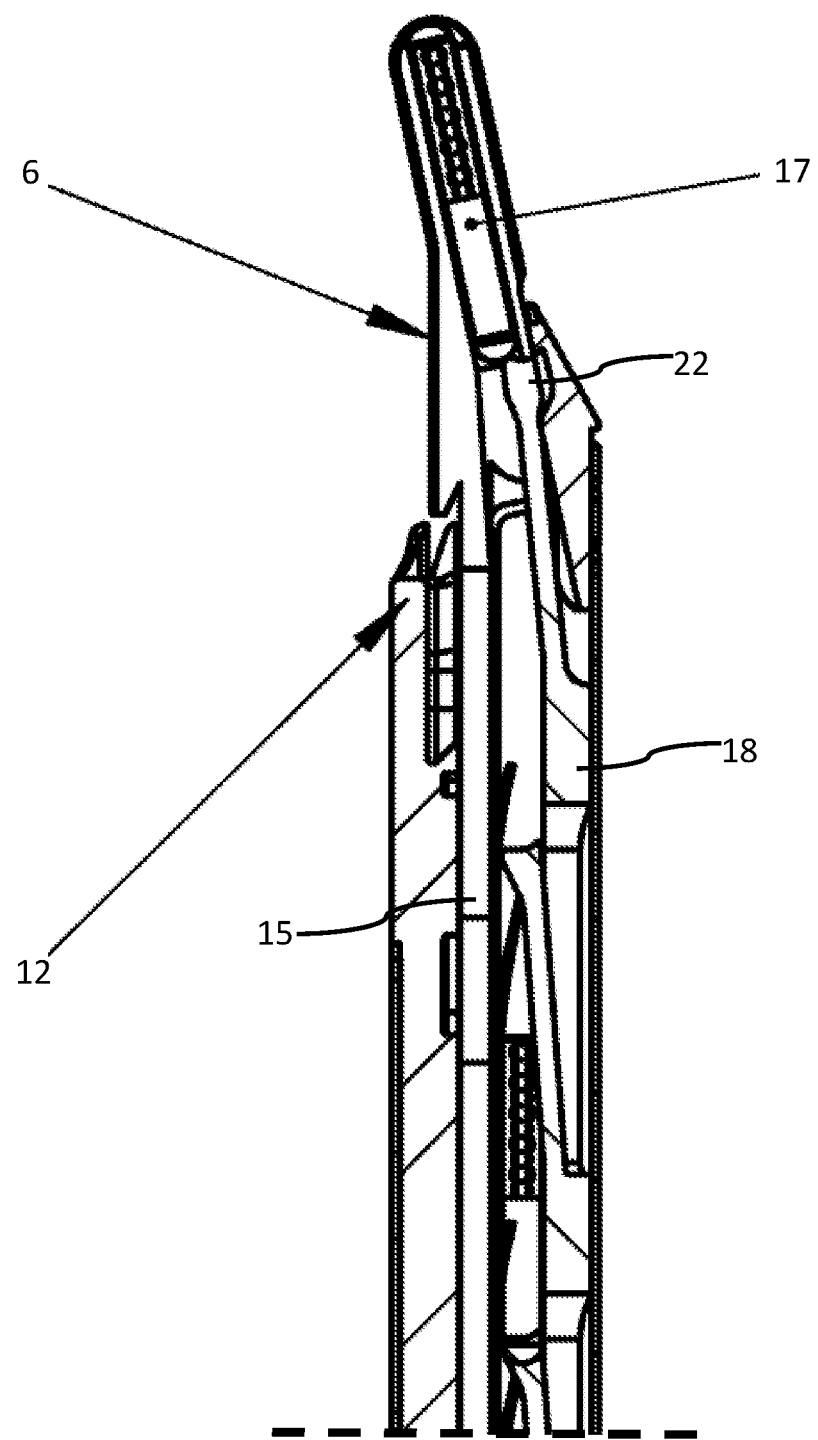
FIG. 15 Illustrates an exploded cross-sectional view of the distal end of the surgical clip cartridge assembly from FIG. 14.
Figure 16:
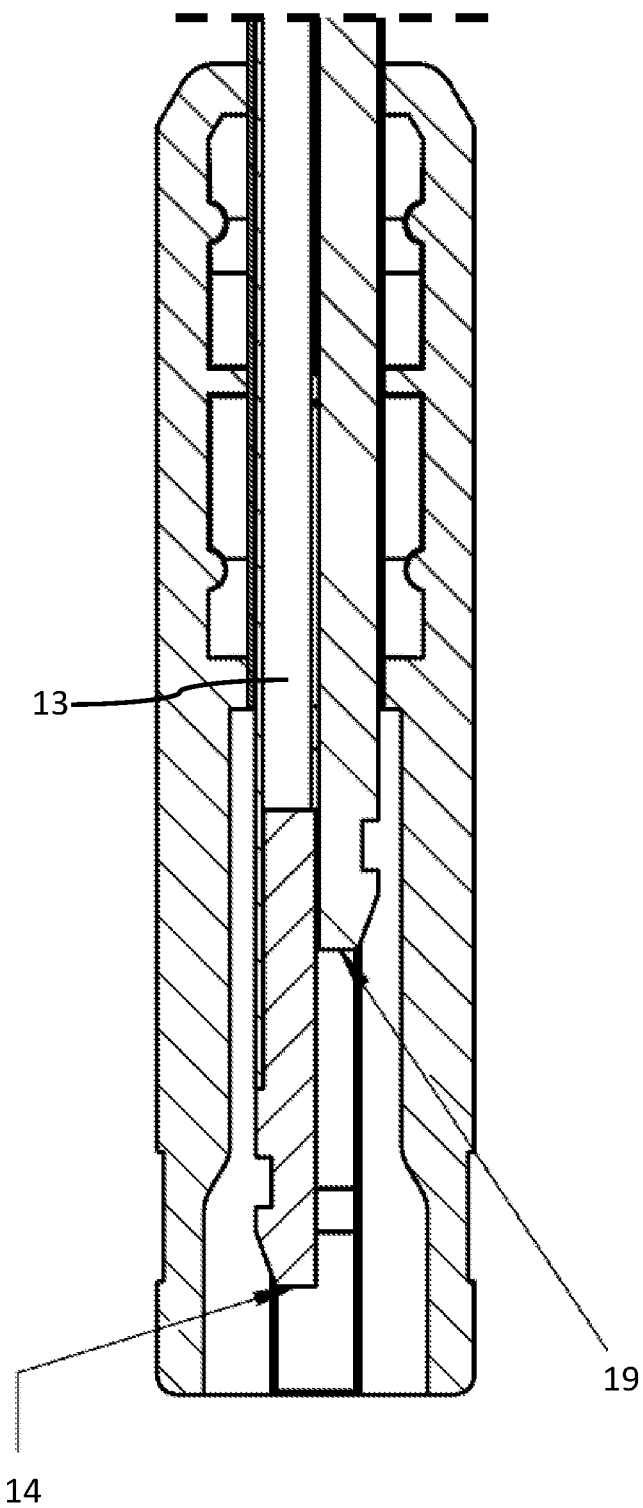
FIG. 16 Illustrates an exploded cross-sectional view of the proximal end of the surgical clip cartridge assembly from FIG. 14.
Figure 17:
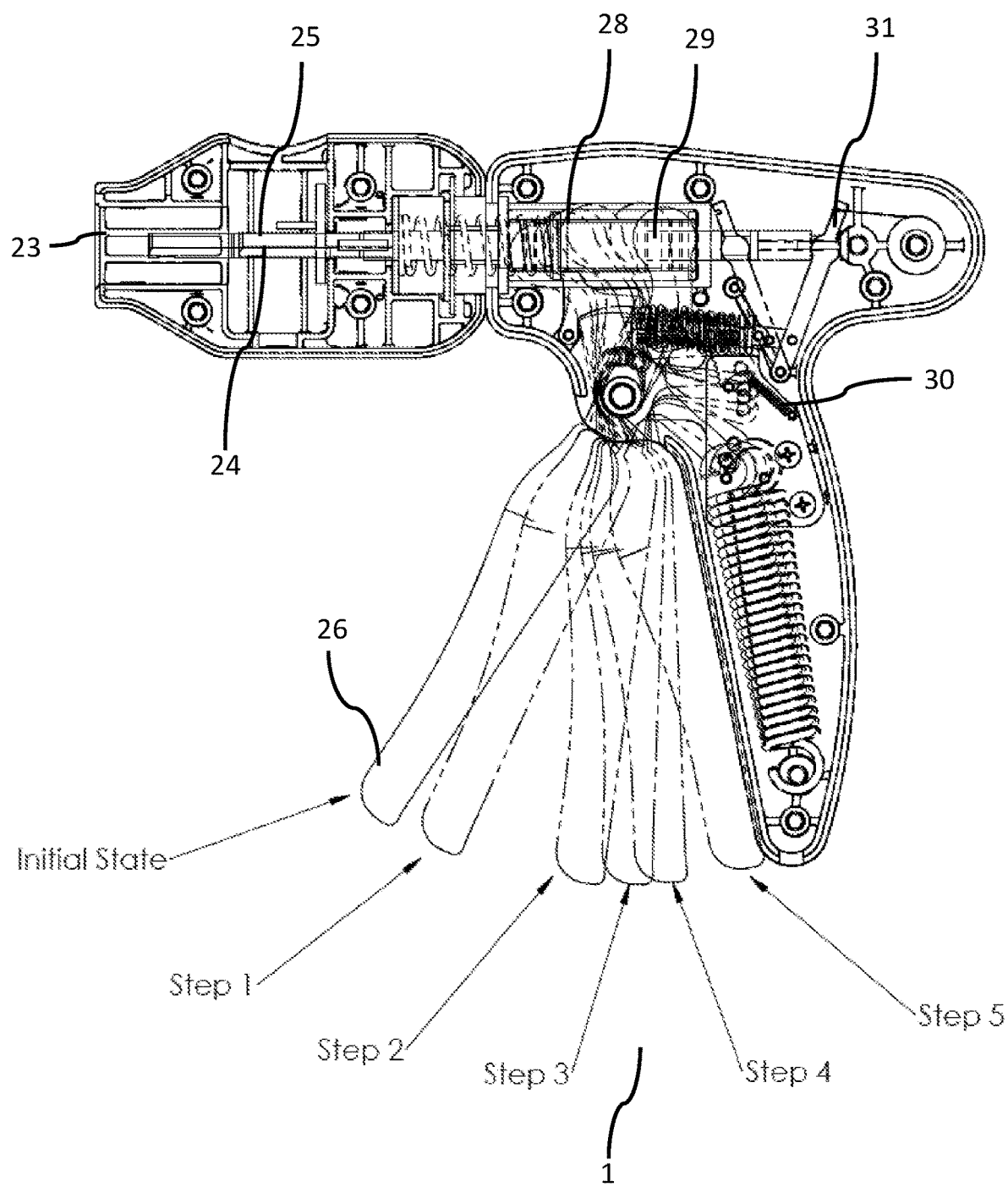
FIG. 17 Illustrates a side cross-sectional view of a surgical clip applier handle showing all trigger positions.
Figure 18:
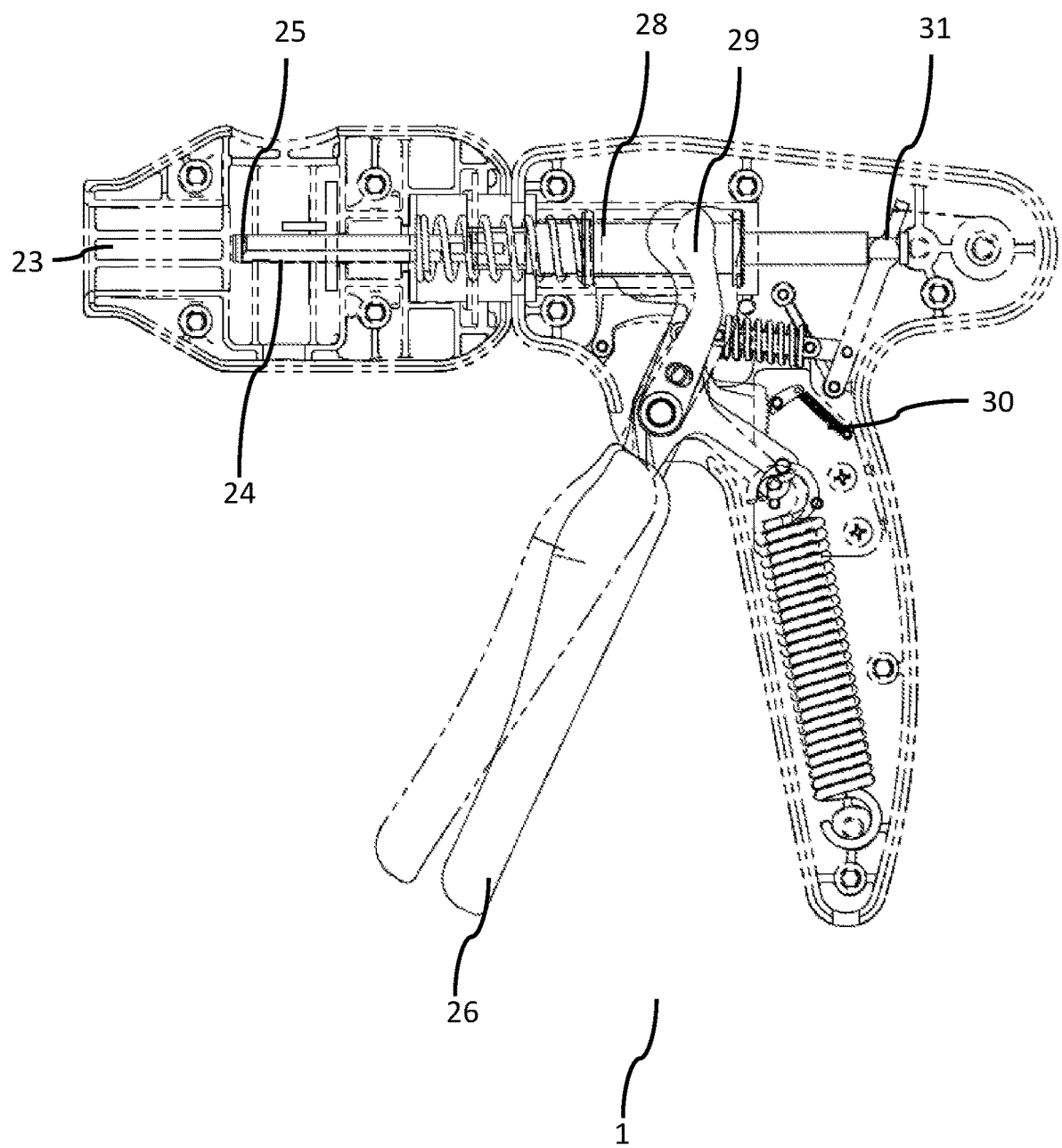
FIG. 18 Illustrates a side cross-sectional view of the surgical clip applier handle showing the initial and step 1 trigger positions.
Figure 19:
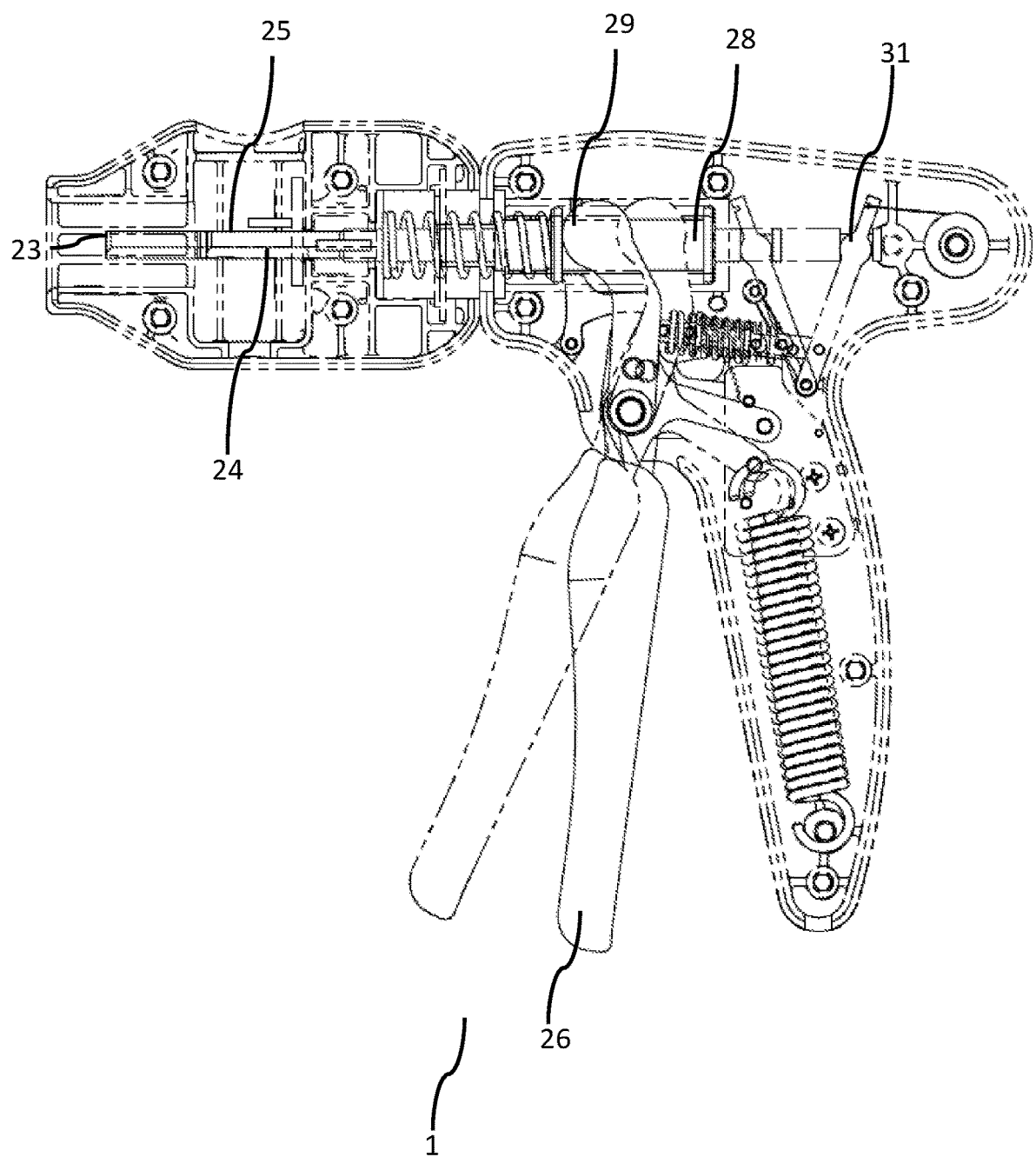
FIG. 19 Illustrates a side cross-sectional view of the surgical clip applier handle showing the step 1 and step 2 trigger positions.
Figure 20:
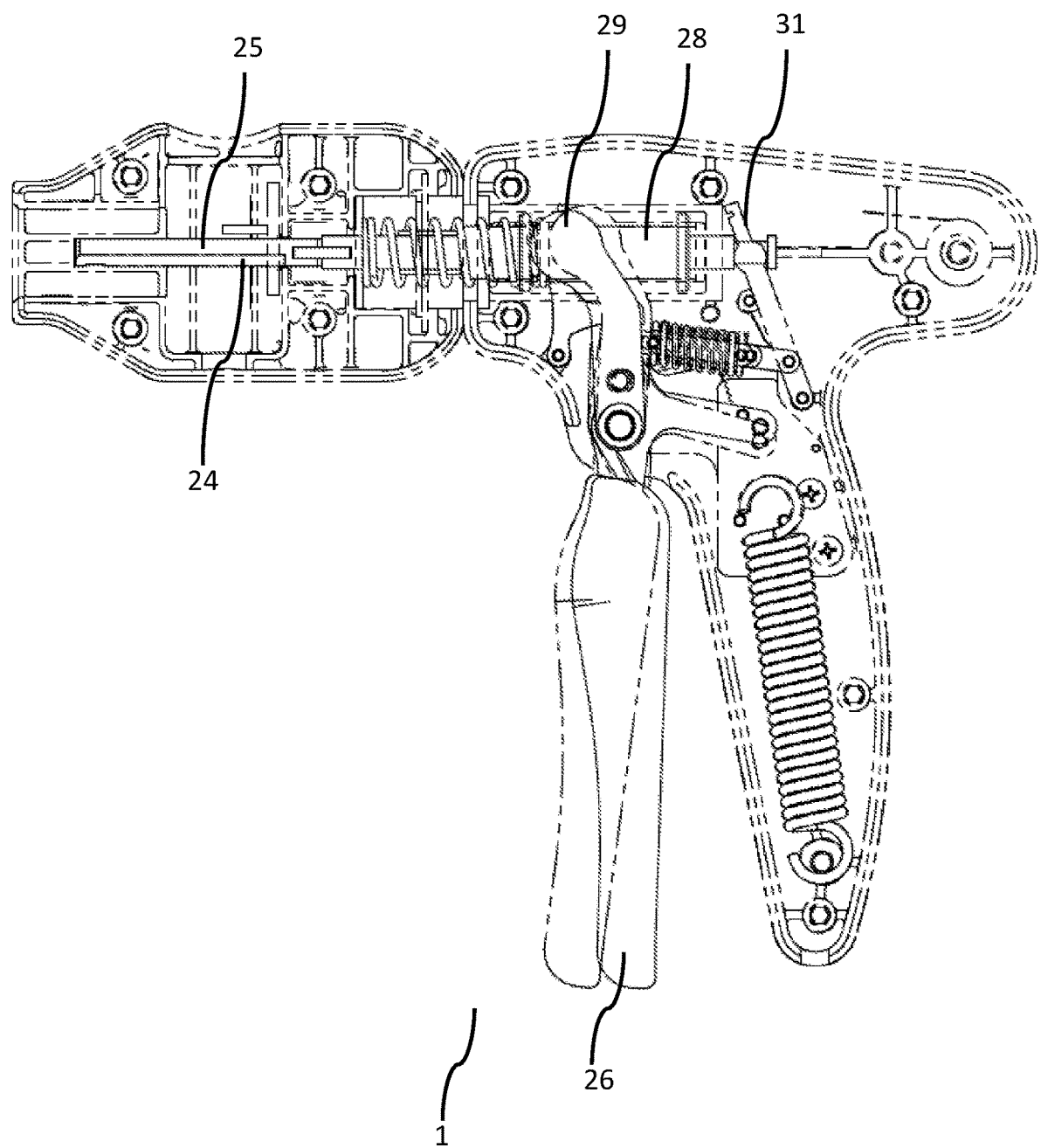
FIG. 20 Illustrates a side cross-sectional view of the surgical clip applier handle showing the step 2 and step 3 trigger positions.
Figure 21:
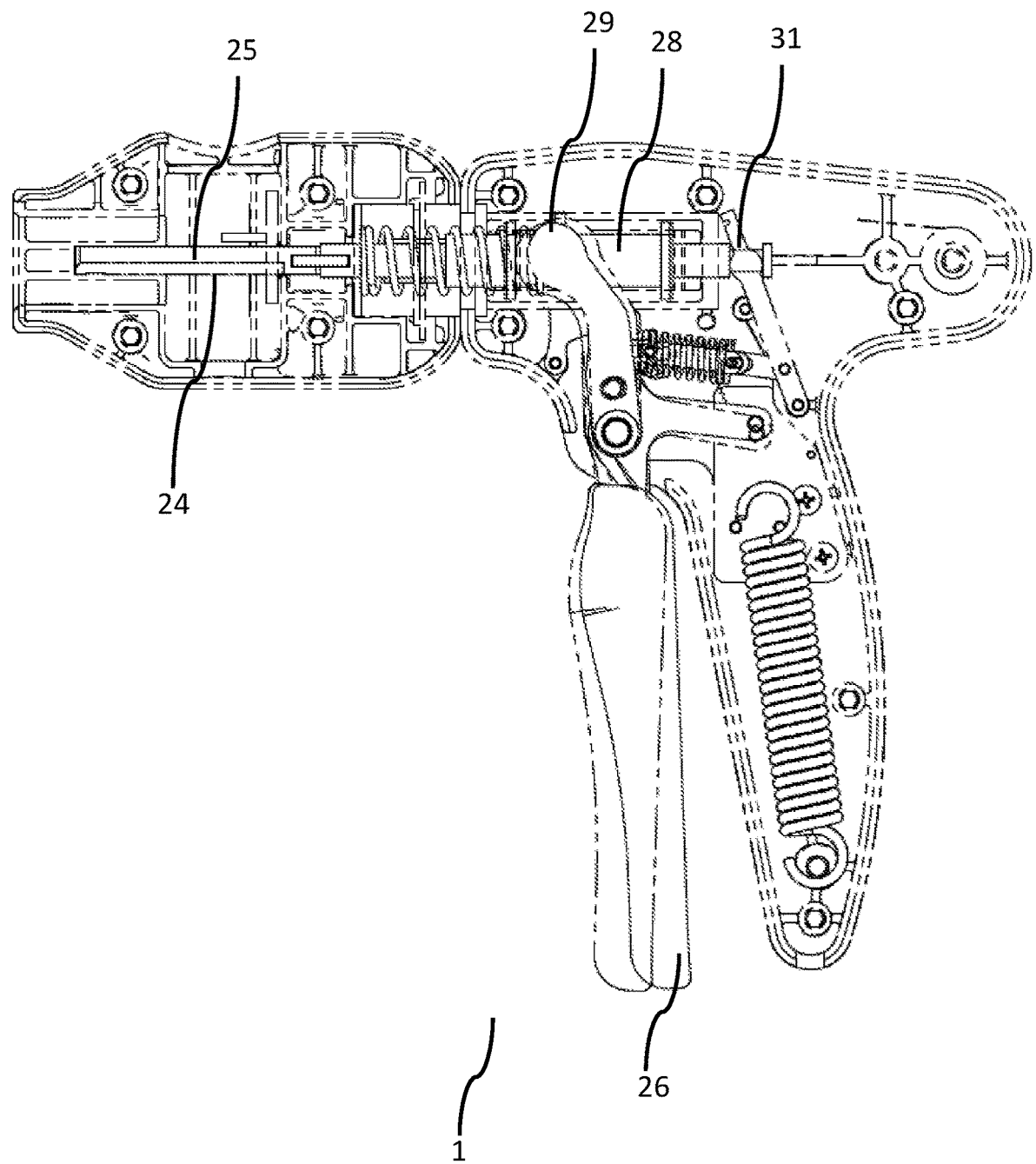
FIG. 21 Illustrates a side cross-sectional view of the surgical clip applier handle showing the step 3 and step 4 trigger positions.
Figure 22:
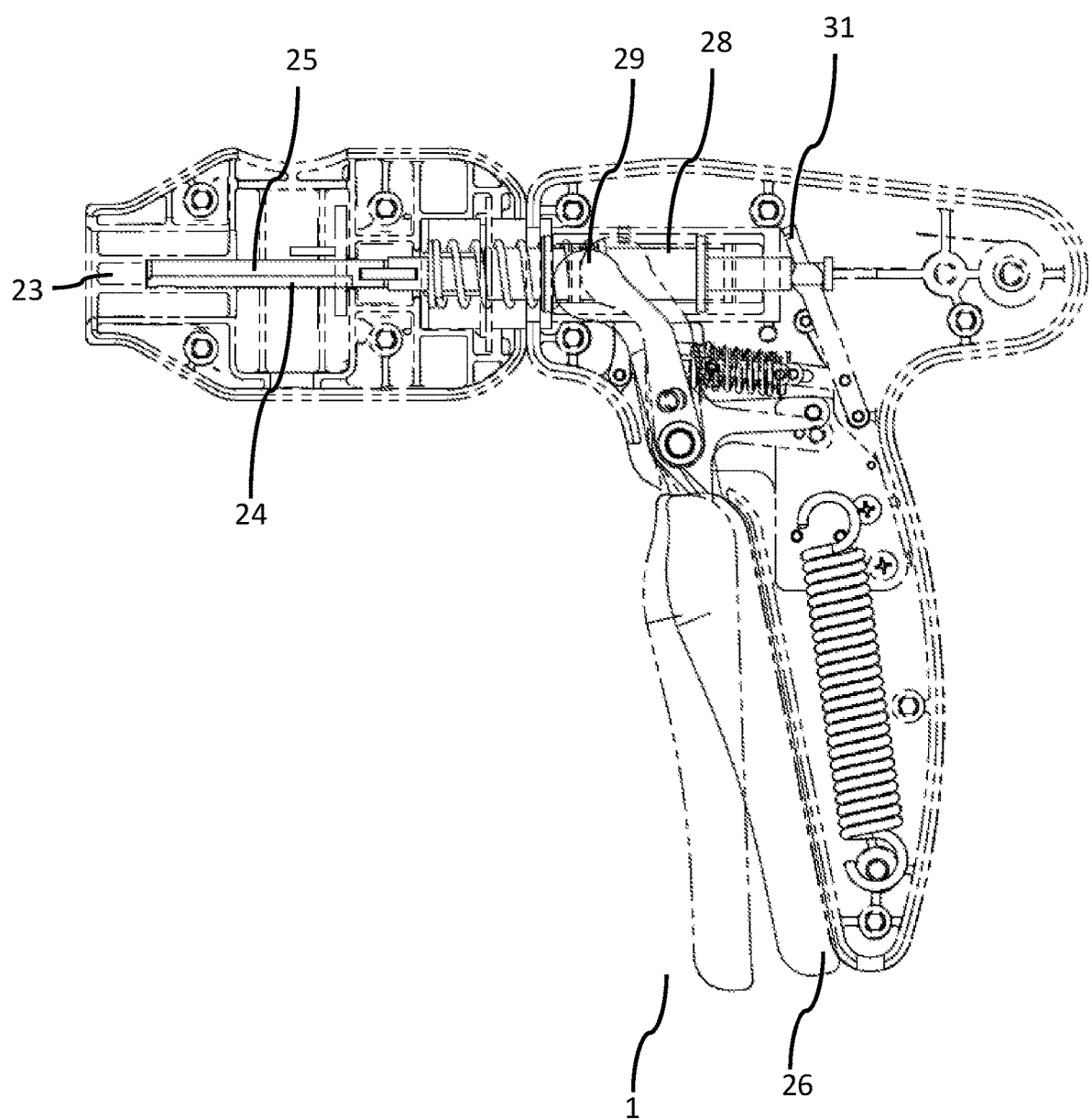
FIG. 22 Illustrates a side cross-sectional view of the surgical clip applier handle showing the step 4 and step 5 trigger positions.
Figure 23:
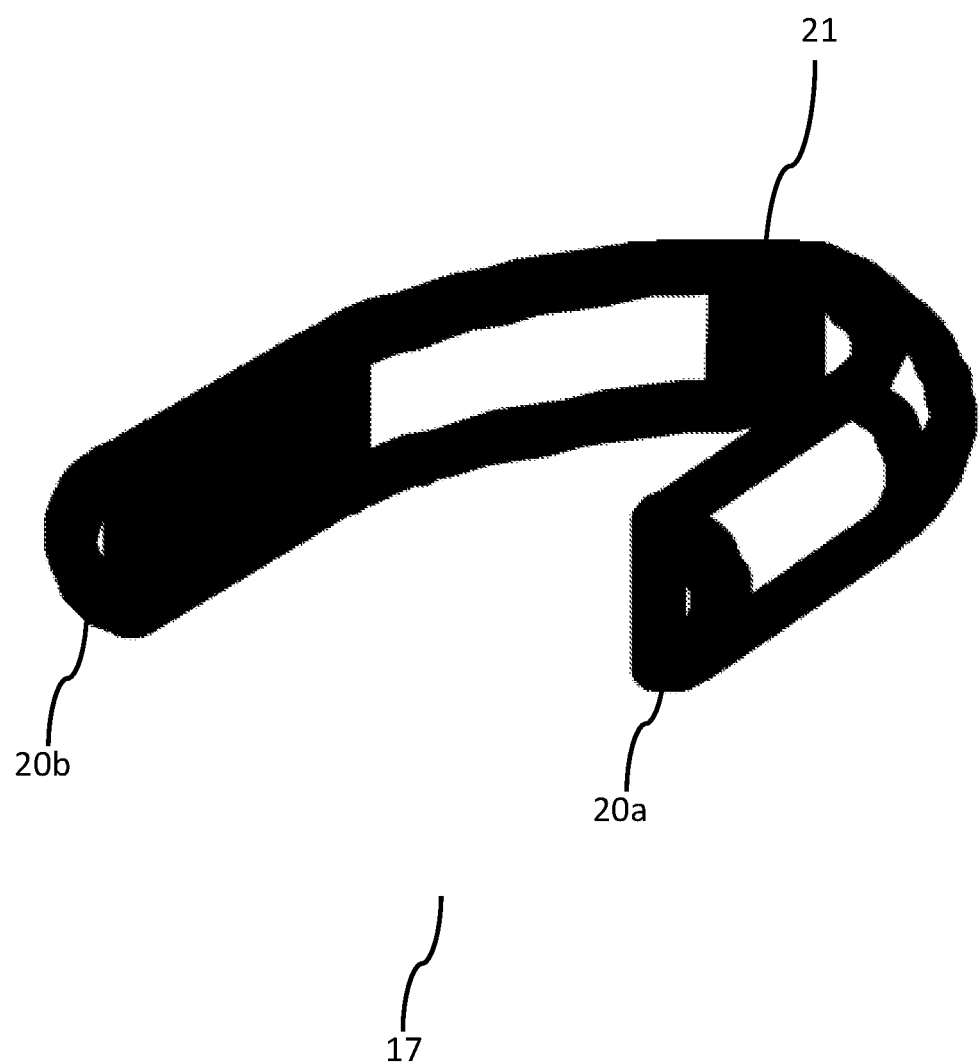
FIG. 23 Illustrates a perspective view of a surgical clip for use with the surgical clip applier.

While several variations of the present invention have been illustrated by way of example in particular embodiments, it is apparent that further embodiments could be developed within the spirit and scope of the present invention. However, it is to be expressly understood that such modifications and adaptations are within the spirit and scope of the present invention, and are inclusive, but not limited to the following appended claims as set forth.

As illustrated in FIGS. 1-22, the subject invention is a surgical clip applier composed of a re-useable handle assembly 1 that is removably attached to a disposable surgical cartridge assembly 2.

As illustrated in FIGS. 1-16, the surgical cartridge assembly 2 comprises an elongated substantially cylindrical tubular housing 3 with a hollow interior, a proximal end 4 that is removably attachable to the handle assembly 1, and a distal end 5 containing surgical clip jaws 6.

The proximal end 4 of the surgical cartridge assembly 2 includes a substantially cylindrical handle adaptor 7 that is formed by a hollow left half adaptor section 8 and a hollow right half adaptor section 9. Hollow left half adaptor section 8 and a hollow right half adaptor section 9 are substantially complementarily shaped to each other. In embodiments of the subject invention, the half adaptor section 8 and right half adaptor section 9 may be attached together by adhesives, fasteners, welding, or other attachment means known to those skilled in the art. The handle adaptor 7 attaches the proximal end 4 of the surgical cartridge assembly 2 to the handle assembly 1.

The distal end of the surgical cartridge assembly 2 contains surgical clip jaws 6 composed of a right jaw 10 and a left jaw 11, illustrated in FIGS. 46-53. The left jaw 11 contains a protruding pin 27a and right jaw 10 contains a protruding pin 27b. The left jaw 11 further contains a curved indentation 32a for receiving and holding a left leg 20a of a surgical clip 17. The right jaw 10 further contains a curved indentation 32b for receiving and holding a left leg 20b of a surgical clip 17.

Proximally to the surgical clip jaws 6, the cartridge assembly 2 contains a curved cinch 12, illustrated in FIGS. 38-41, which extends along the axis of the cartridge assembly 2 within the tubular housing 3. The bottom surface of the cinch 12 contains a jaw leg guide 33 comprising an indentation 34 with a substantially triangular shaped protrusion 35. The protruding pin 27a of the left jaw 11 and the protruding pin 27b of the right jaw 10 move through the jaw leg guide 33, between the indentation 34 with the triangular shaped protrusion 35 during operation of the device.

Figure 24:
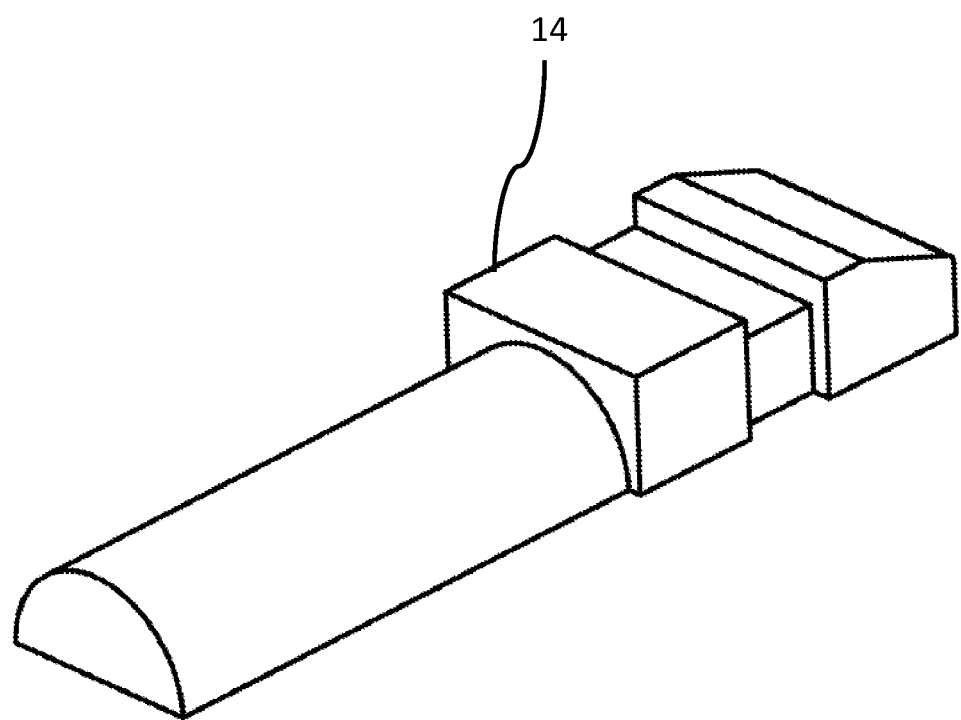
FIG. 24 Illustrates a perspective view of the cinch handle interface of the surgical clip cartridge assembly.
Figure 25:
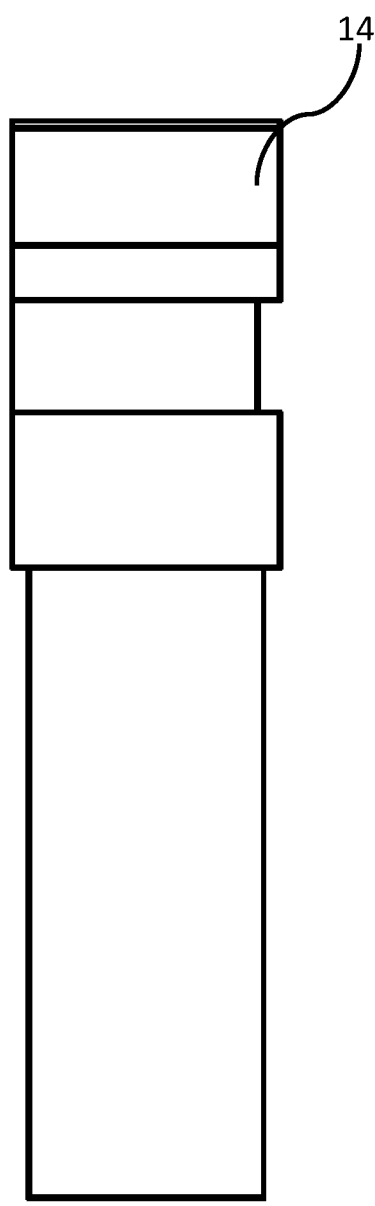
FIG. 25 Illustrates a top view of the cinch handle interface of the surgical clip cartridge assembly.
Figure 26:
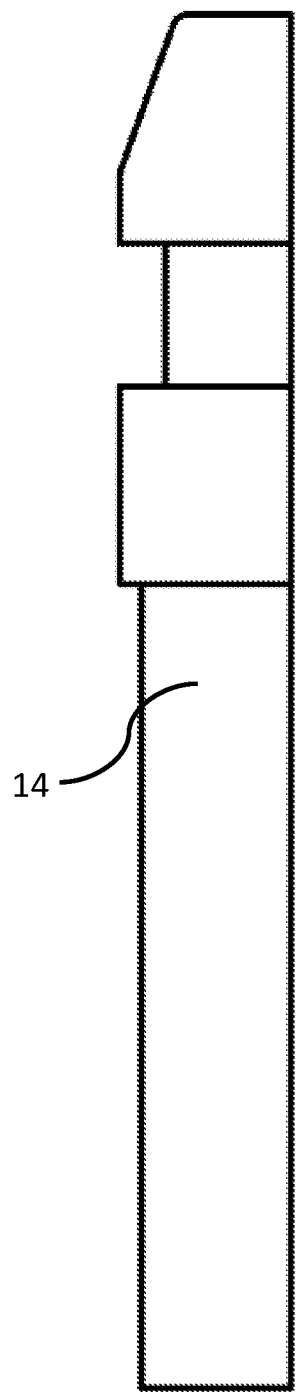
FIG. 26 Illustrates a side view of the cinch handle interface of the surgical clip cartridge assembly.
Figure 27:
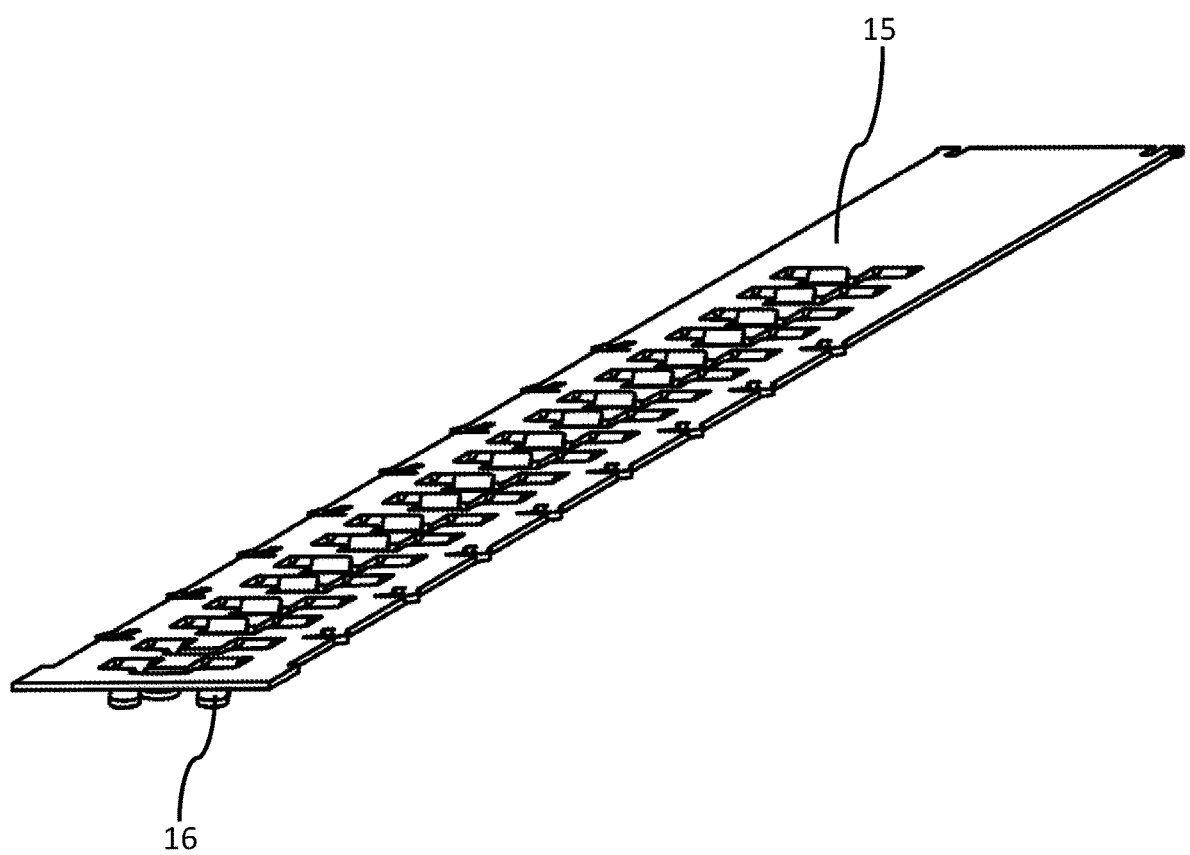
FIG. 27 Illustrates a perspective view of the clip retainer of the surgical clip cartridge assembly.
Figure 28:
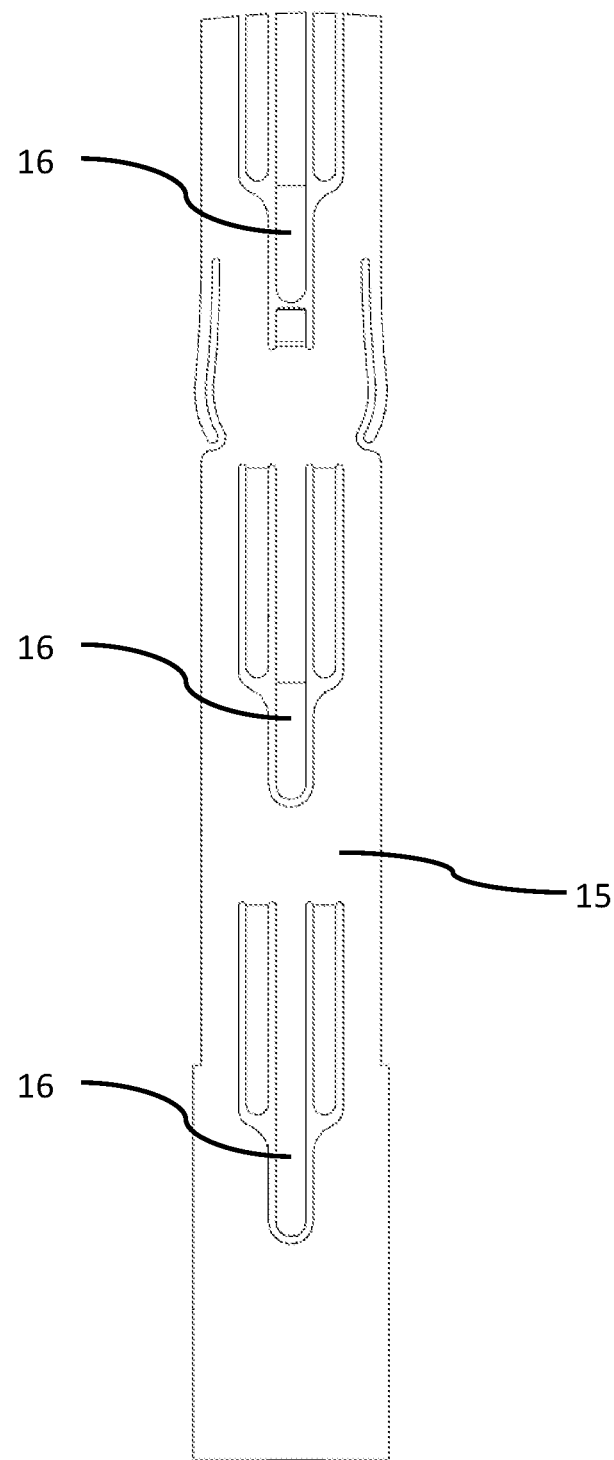
FIG. 28 Illustrates a top view of the clip retainer of the surgical clip cartridge assembly.
Figure 29:
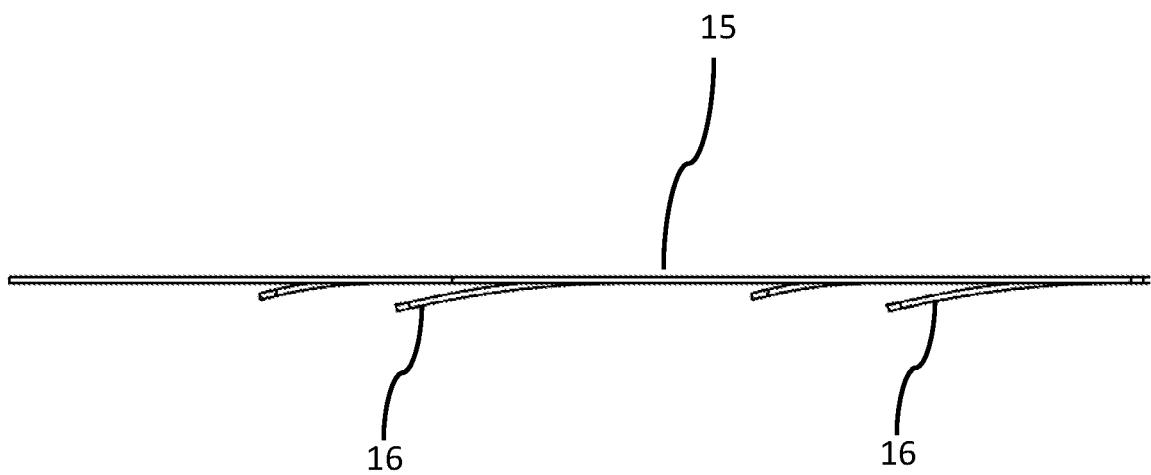
FIG. 29 Illustrates a side view of the clip retainer of the surgical clip cartridge assembly.
Figure 30:
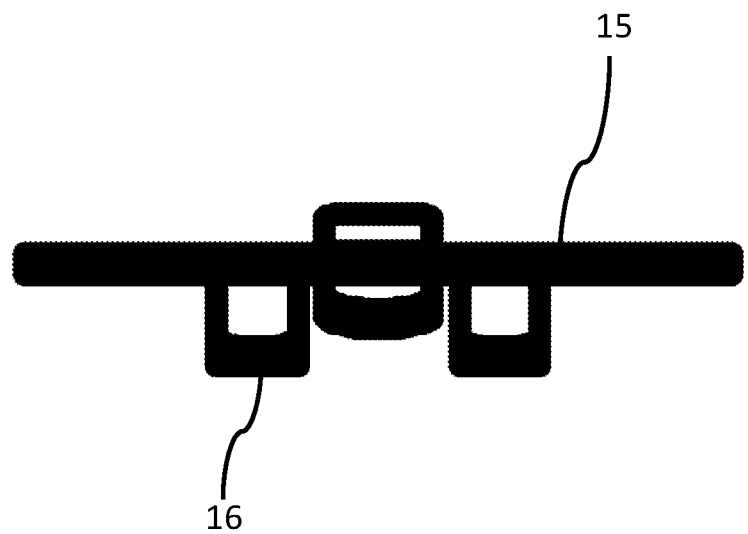
FIG. 30 Illustrates a front view of the clip retainer of the surgical clip cartridge assembly.

Proximally to the cinch 12, the cartridge assembly 2 contains a curved cinch pusher 13, illustrated in FIGS. 42-45, which extends along the axis of the cartridge assembly 2 within the tubular housing 3 to the proximal end 4. A cinch handle interface 14, illustrated in FIGS. 24-26, is located at the proximal end of the cinch pusher 13.

Below the surgical clip jaws 6, the cinch 12, and the cinch pusher 13, the cartridge assembly 2 contains a surgical clip retainer 15, illustrated in FIGS. 27-30, that extends along the axis of the cartridge assembly 2 within the tubular housing 3 to the proximal end 4. The surgical clip retainer 15 contains a plurality of sequentially centrally aligned spring tabs 16 that extend downward.

Below the surgical clip retainer 15, the cartridge assembly 2 contains a plurality of substantially flat surgical clips 17 extending along the axis of the cartridge assembly 2 within the tubular housing 3. In embodiments of the subject invention, each surgical clip 17 has a generally U-shaped configuration in the open or uncompressed position before attachment over a blood vessel to ligate that vessel. In other embodiments of the subject invention, the surgical clip 17 may have a generally V-shaped configuration. Each surgical clip 17 includes a pair of opposed elongated ligating legs 20a and 20b that have substantially uniform widths and lengths. Ligating legs 20a and 20b may be substantially mirror images of each other. The proximal ends of the ligating legs curve towards each other to form an apex connection 21. The apex connection 21 of each surgical clip 17 is relatively deformable to allow the opposed elongated ligating legs 20a and 20b to compress inwards towards one another when the appropriate force is applied to the external surface of each ligating leg 20a and 20b by the surgical jaws 6.

Figure 31:
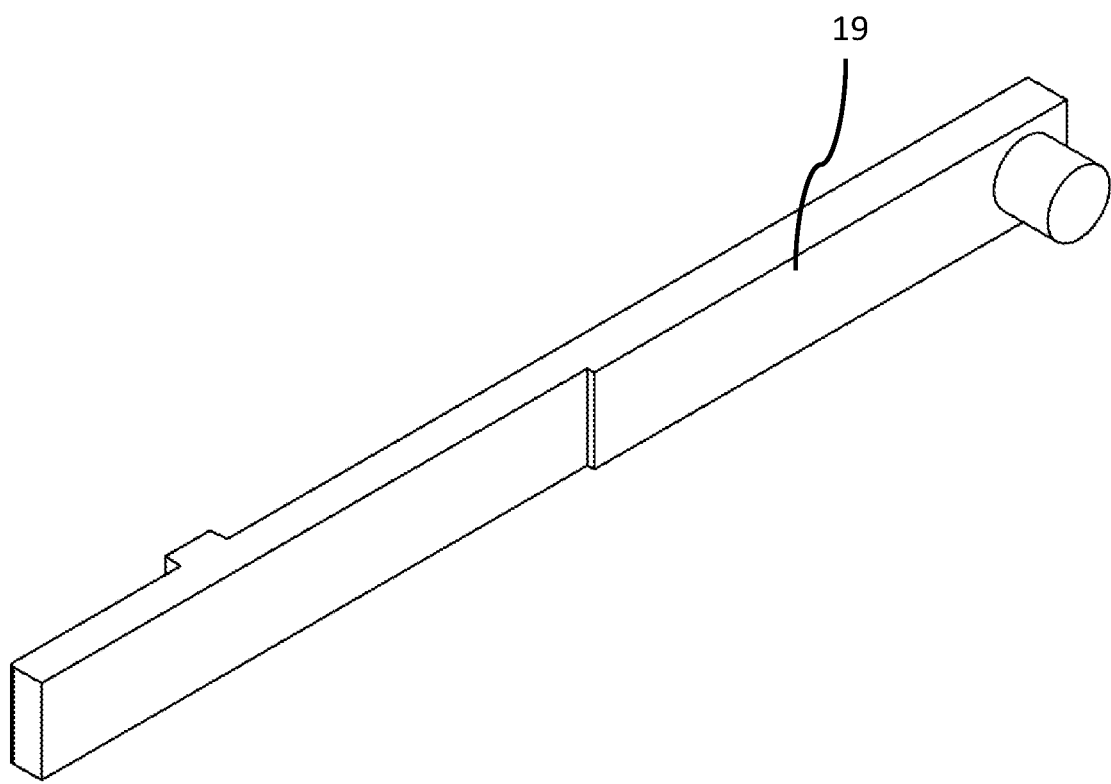
FIG. 31 Illustrates a perspective view of the flexure lock pusher of the surgical clip cartridge assembly.
Figure 32:
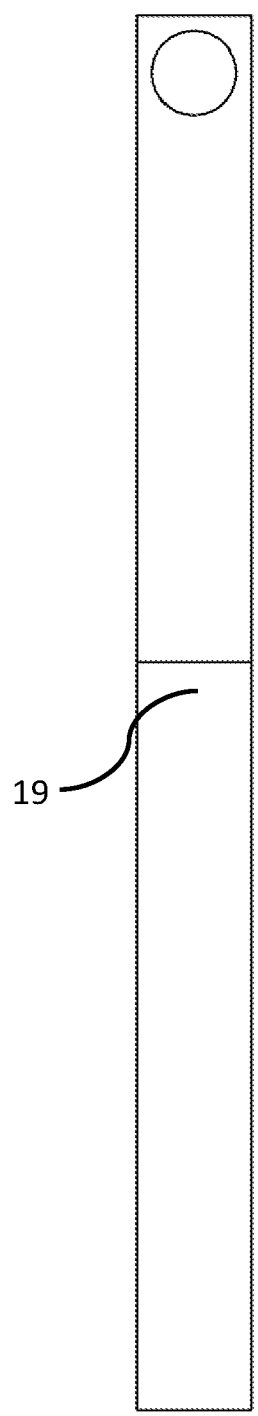
FIG. 32 Illustrates a top view of the flexure lock pusher of the surgical clip cartridge assembly.
Figure 33:
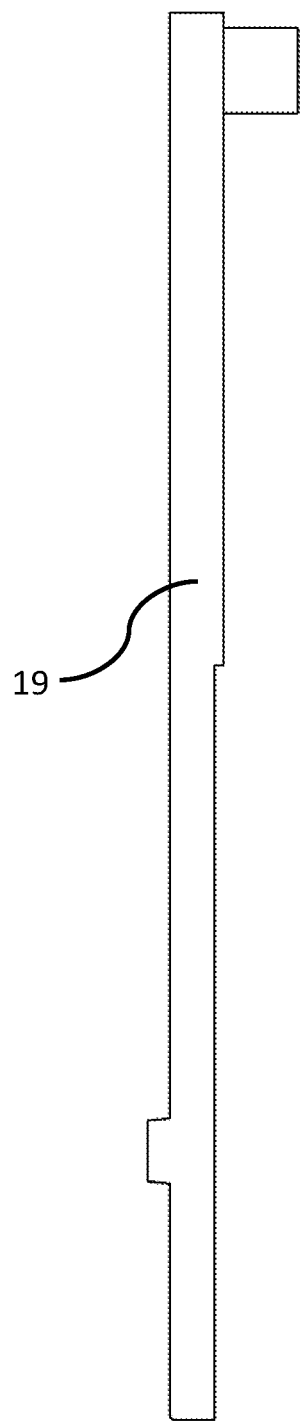
FIG. 33 Illustrates a side view of the flexure lock pusher of the surgical clip cartridge assembly.
Figure 34:
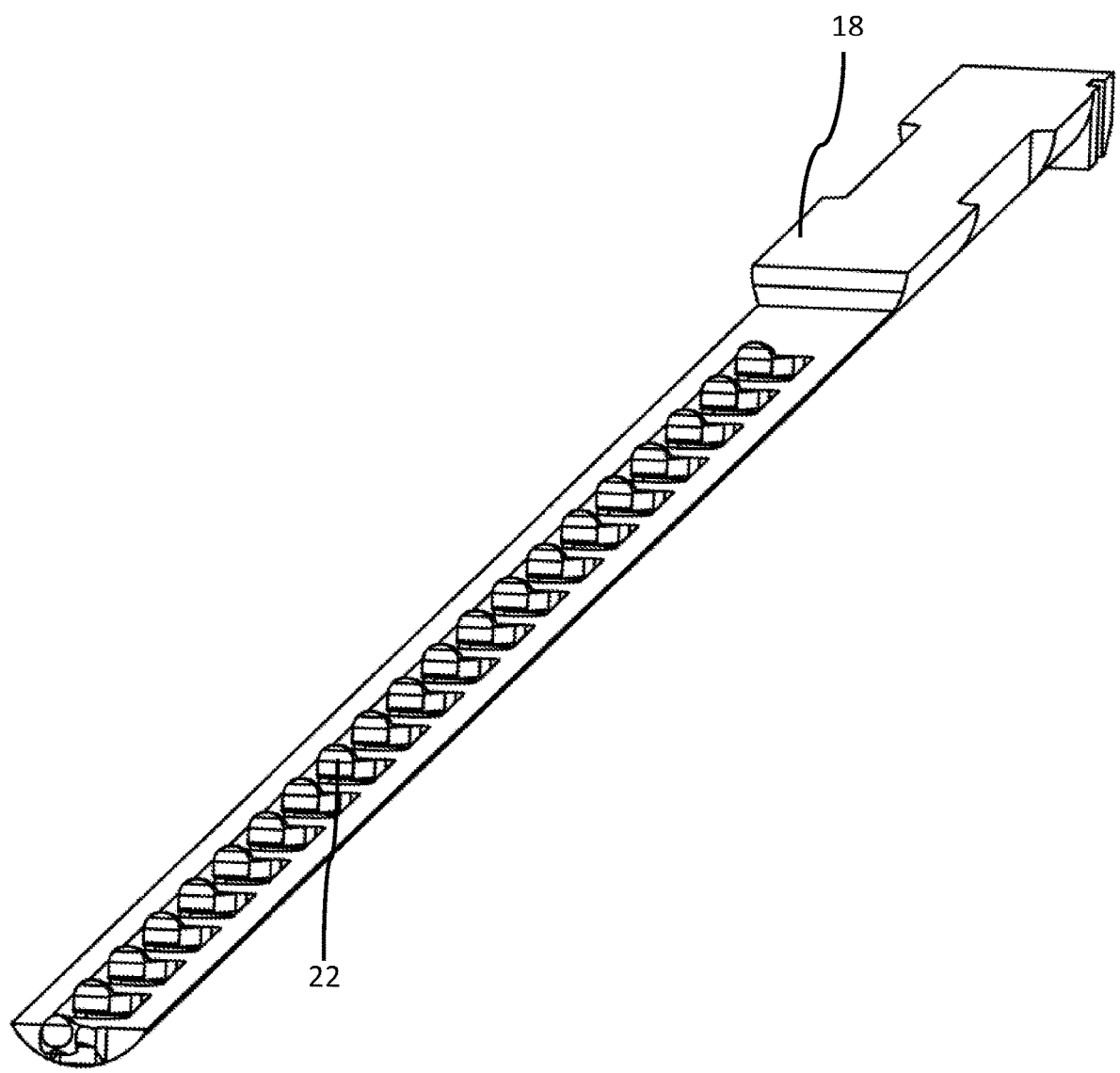
FIG. 34 Illustrates a perspective view of the surgical clip pusher of the surgical clip cartridge assembly.
Figure 35:
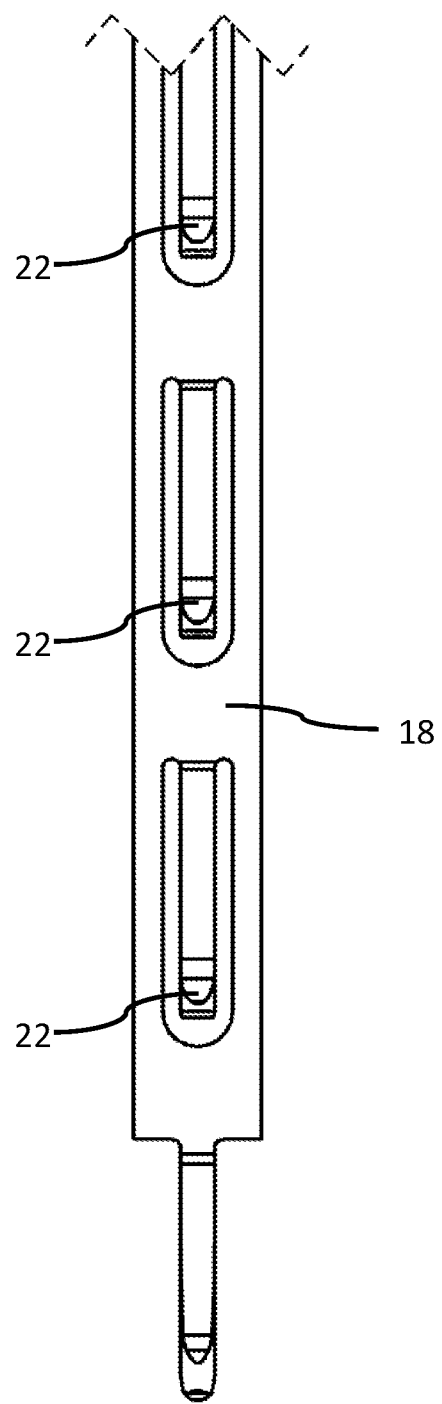
FIG. 35 Illustrates a top view of the surgical clip pusher of the surgical clip cartridge assembly.
Figure 36:
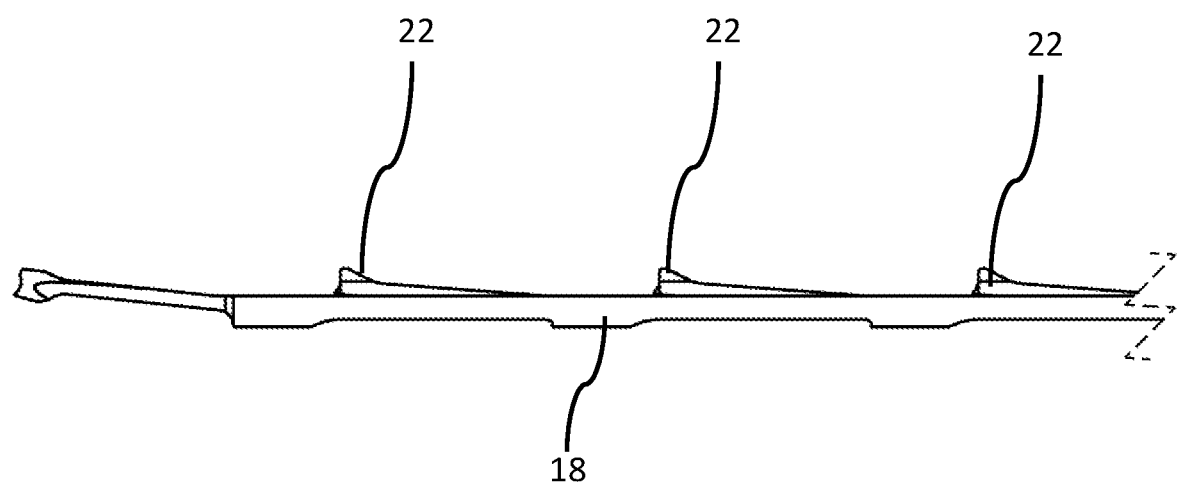
FIG. 36 Illustrates a side view of the surgical clip pusher of the surgical clip cartridge assembly.
Figure 37:
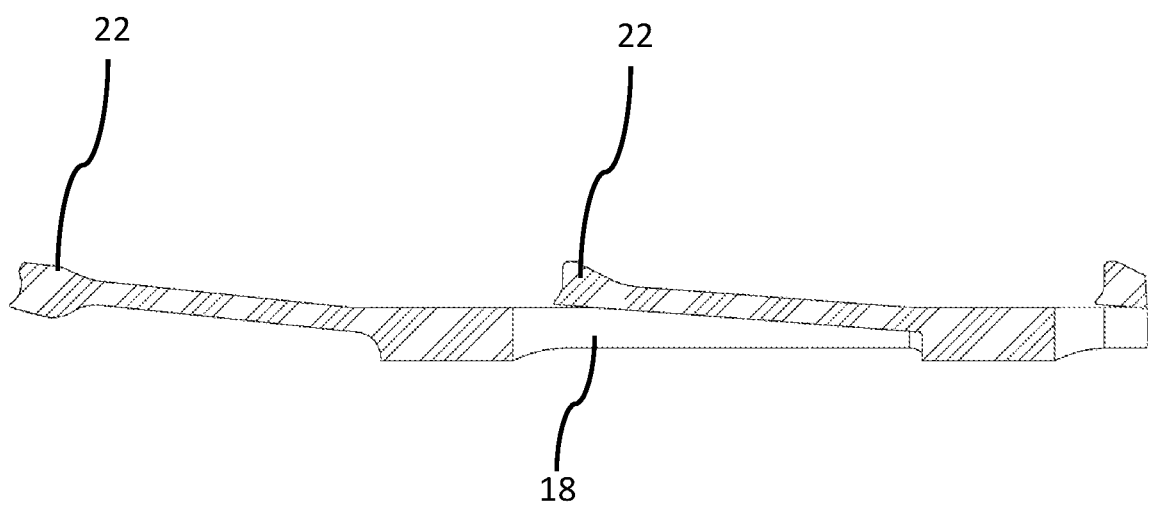
FIG. 37 Illustrates a side cross-sectional view of the surgical clip pusher of the surgical clip cartridge assembly.
Figure 38:
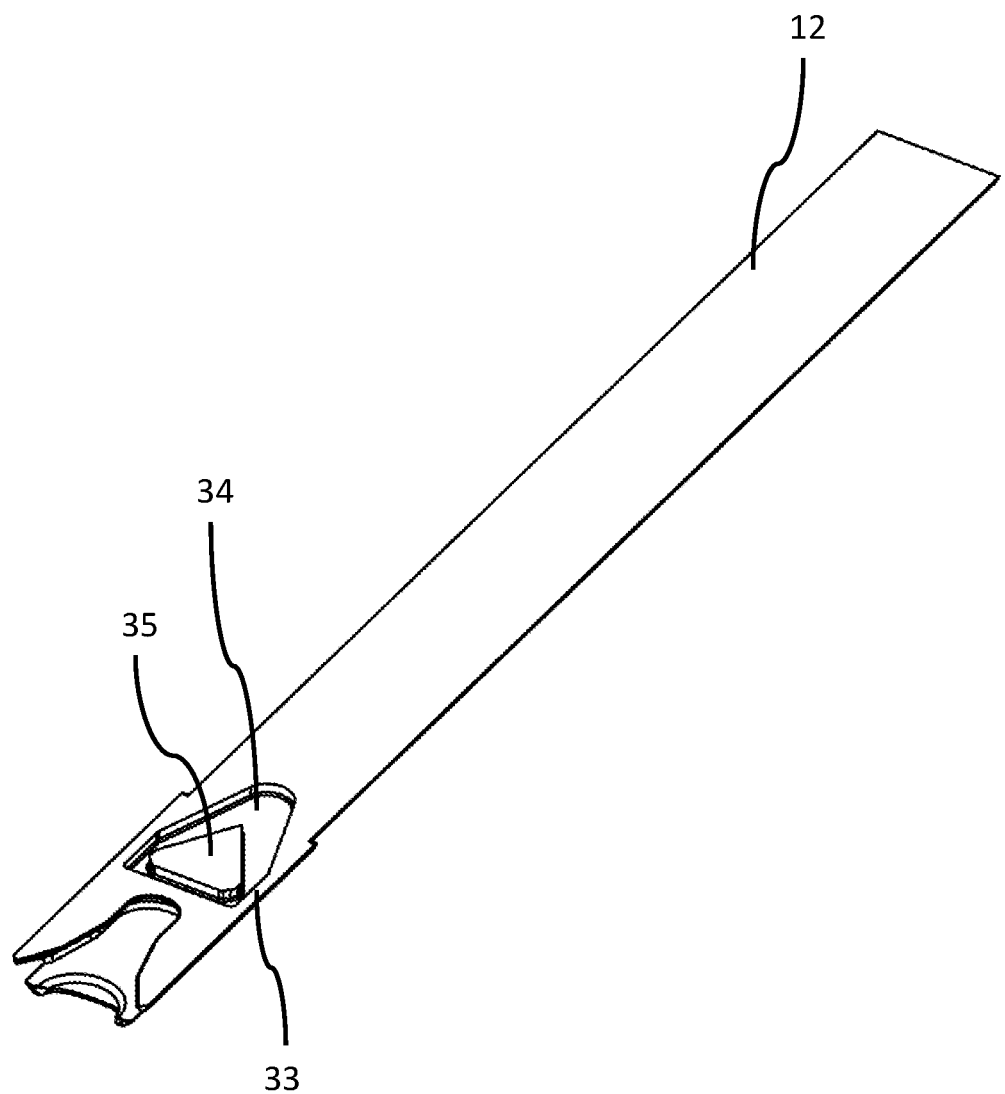
FIG. 38 Illustrates a perspective view of the cinch of the surgical clip cartridge assembly.
Figure 39:
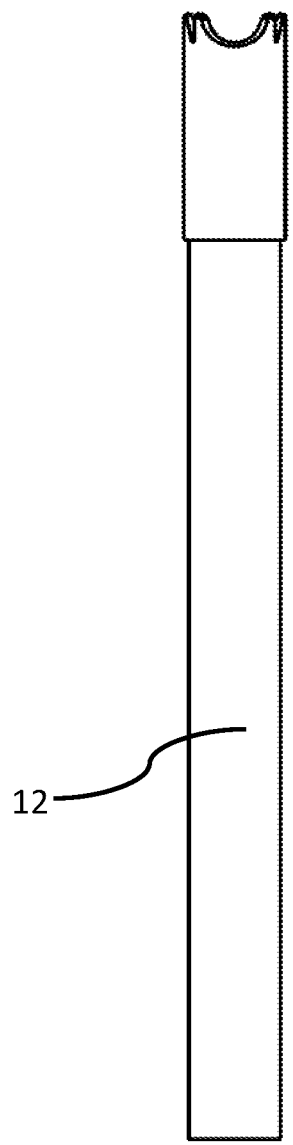
FIG. 39 Illustrates a top view of the cinch of the surgical clip cartridge assembly.
Figure 40:
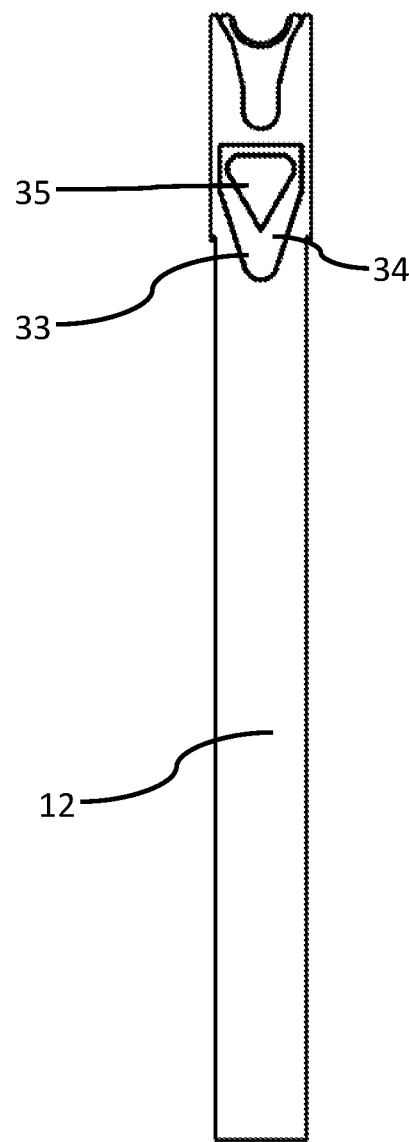
FIG. 40 Illustrates a bottom view of the cinch of the surgical clip cartridge assembly.
Figure 41:
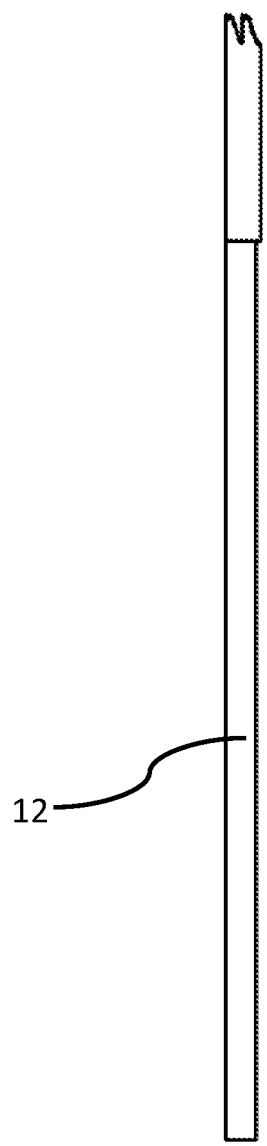
FIG. 41 Illustrates a side view of the cinch of the surgical clip cartridge assembly.
Figure 42:
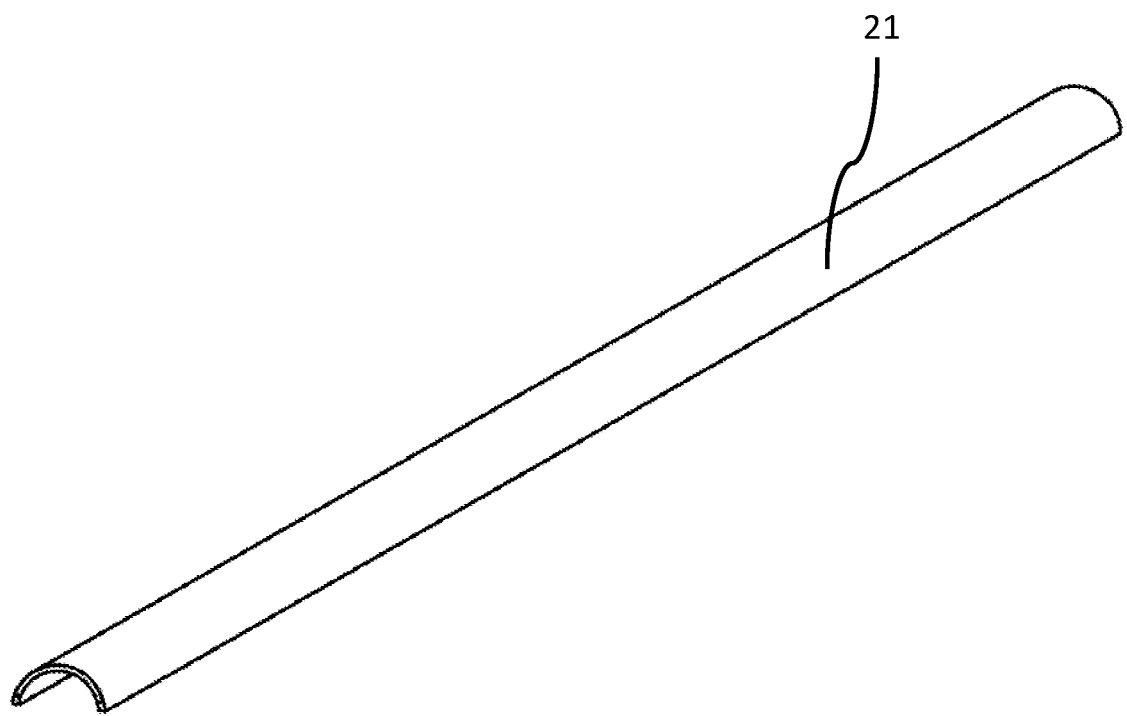
FIG. 42 Illustrates a perspective view of the cinch pusher of the surgical clip cartridge assembly.
Figure 43:
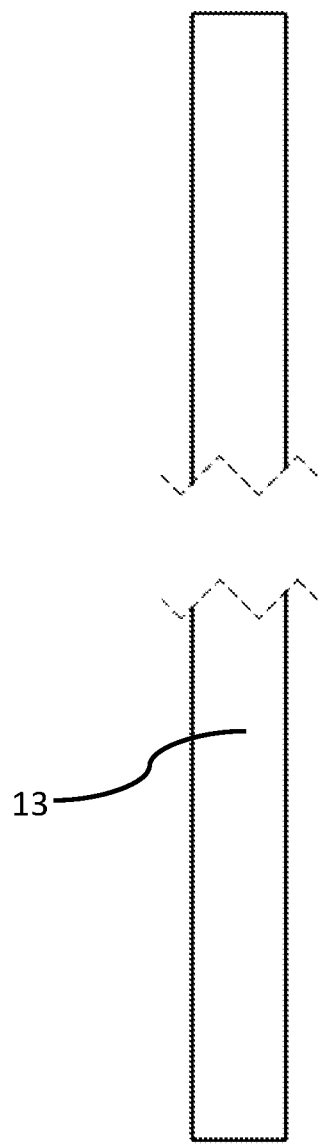
FIG. 43 Illustrates a top view of the cinch of the surgical clip cartridge assembly.
Figure 44:
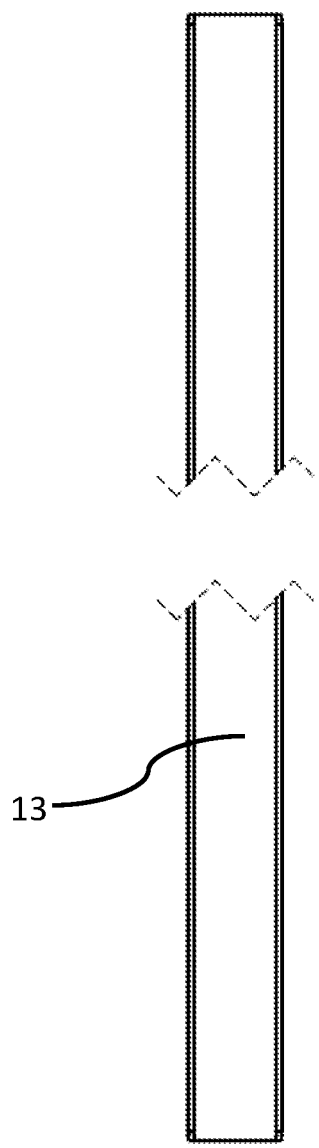
FIG. 44 Illustrates a bottom view of the cinch of the surgical clip cartridge assembly.
Figure 45:
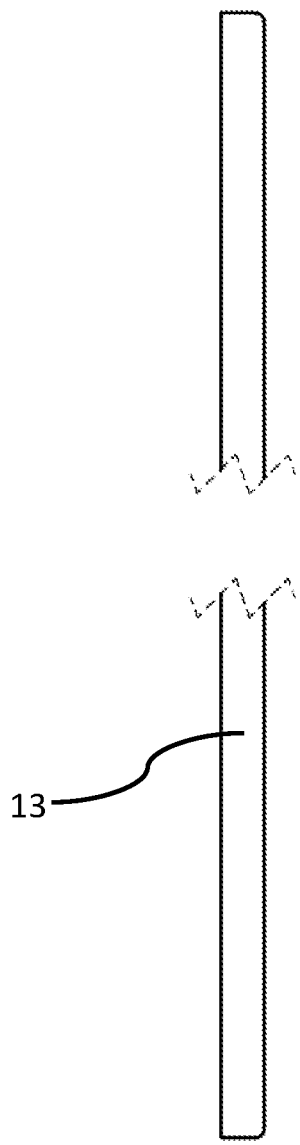
FIG. 45 Illustrates a side view of the cinch of the surgical clip cartridge assembly.
Figure 46:
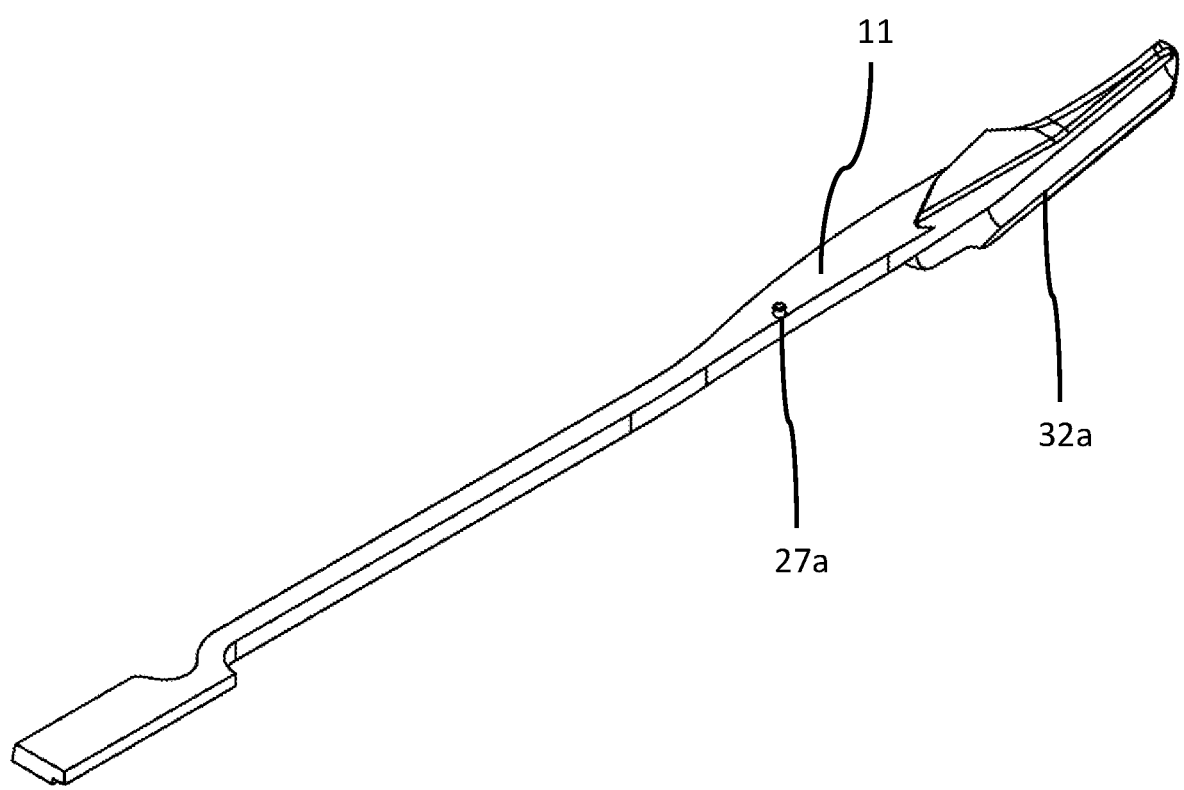
FIG. 46 Illustrates a perspective view of the left jaw of the surgical clip cartridge assembly.
Figure 47:
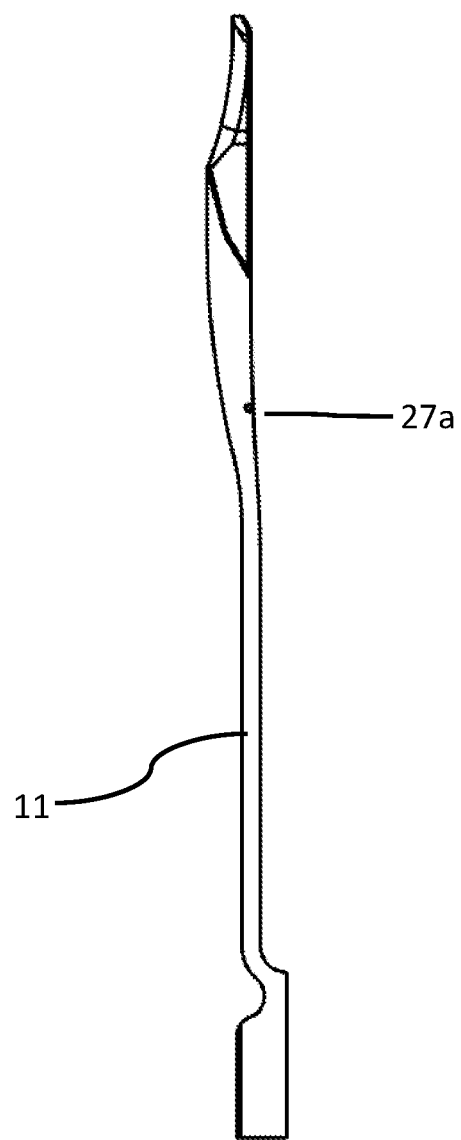
FIG. 47 Illustrates a top view of the left jaw of the surgical clip cartridge assembly.
Figure 48:
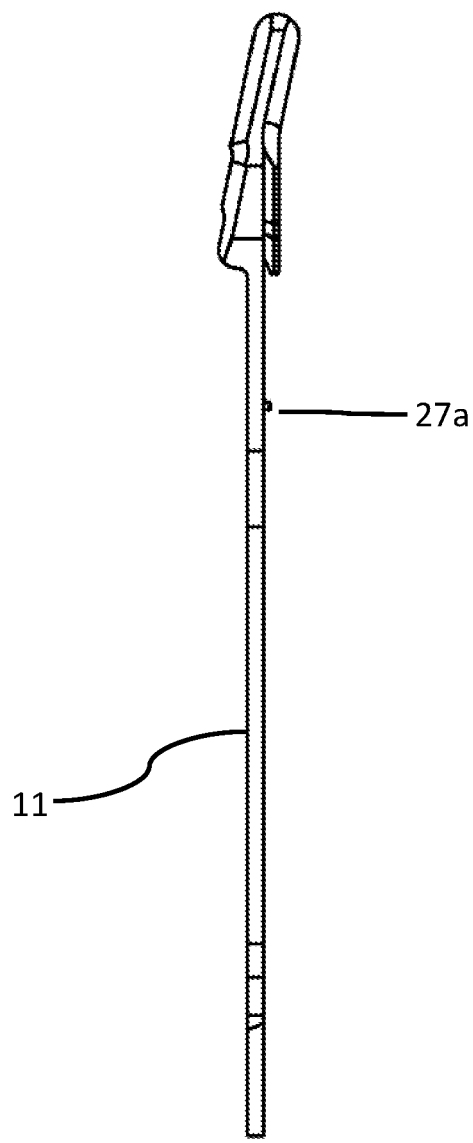
FIG. 48 Illustrates a left side view of the left jaw of the surgical clip cartridge assembly.
Figure 49:
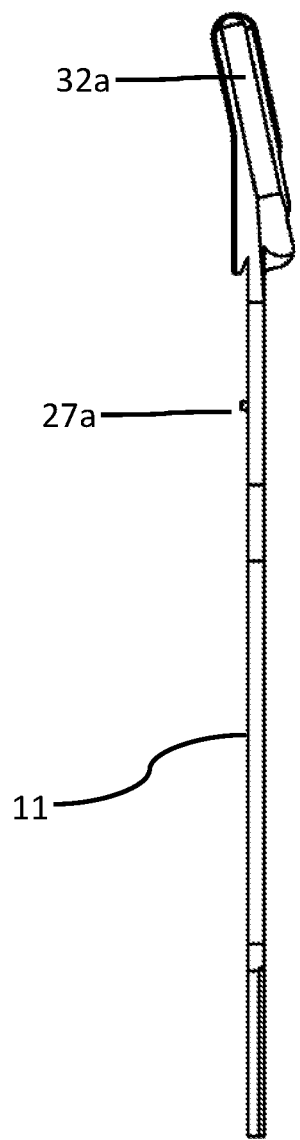
FIG. 49 Illustrates a right-side view of the left jaw of the surgical clip cartridge assembly.
Figure 50:
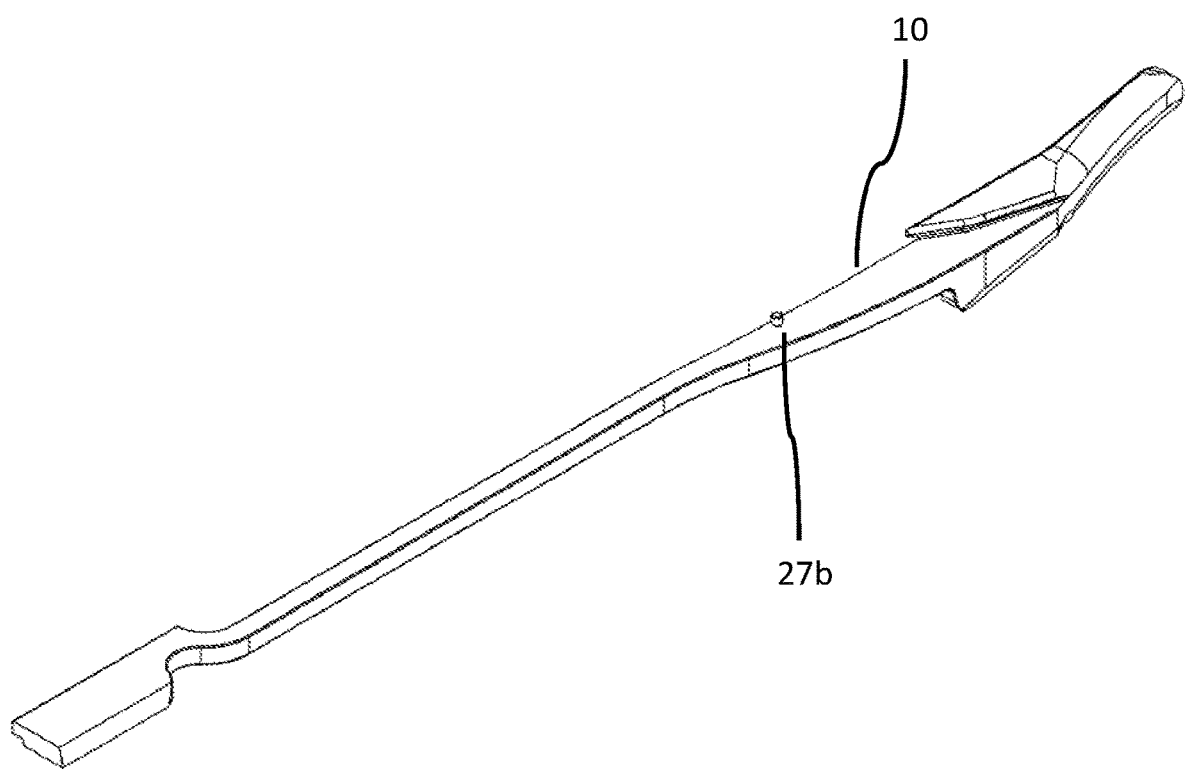
FIG. 50 Illustrates a perspective view of the right jaw of the surgical clip cartridge assembly.
Figure 51:
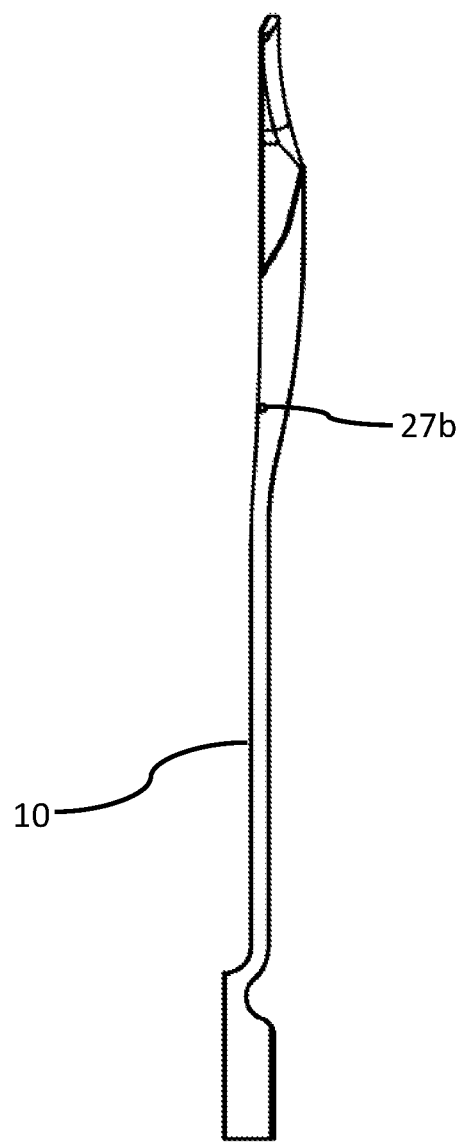
FIG. 51 Illustrates a top view of the right jaw of the surgical clip cartridge assembly.
Figure 52:
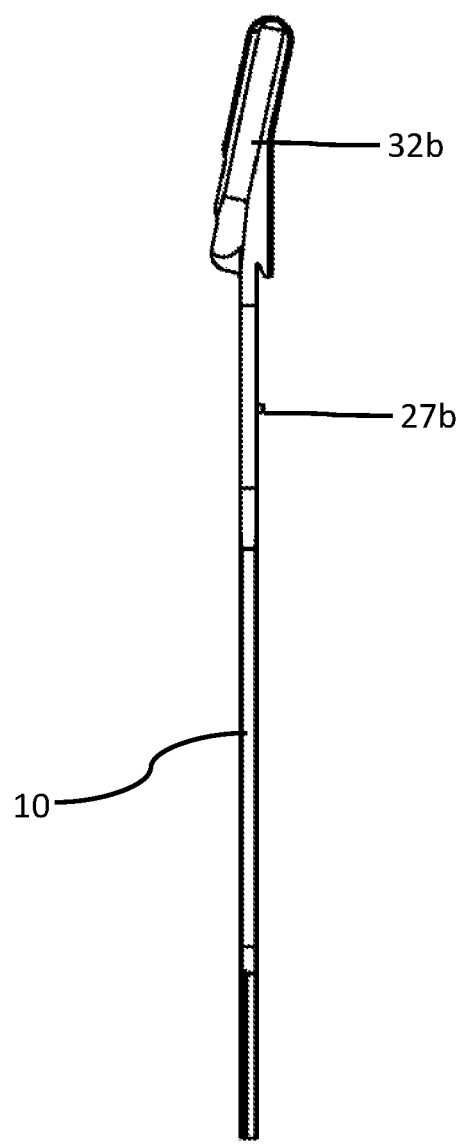
FIG. 52 Illustrates a left side view of the right jaw of the surgical clip cartridge assembly.
Figure 53:
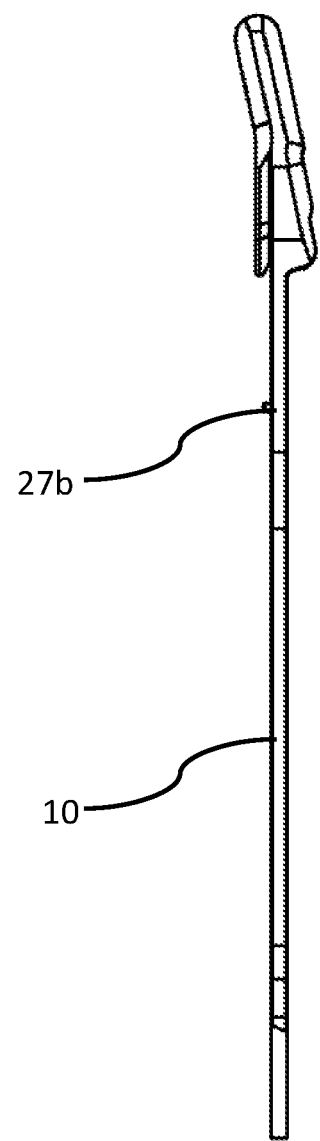
FIG. 53 Illustrates a right-side view of the right jaw of the surgical clip cartridge assembly.

Below the surgical clip retainer 15 and the plurality of substantially flat surgical clips 17, the cartridge assembly 2 contains a surgical clip pusher 18, illustrated in FIGS. 34-37, that extends along the axis of the cartridge assembly 2 within the tubular housing 3. A flexure lock pusher 19, illustrated in FIGS. 31-33, is located at the proximal end of the surgical clip pusher 18. The top surface of the surgical clip pusher 18 contains a plurality of upward tabs 22 that are configured to hold the apex connection 21 of each surgical clip 17.

The plurality of substantially flat surgical clips 17 are contained between the spring tabs 16 of the surgical clip retainer 15 and the plurality of upward tabs 22 of the surgical clip pusher 18. In embodiments of the subject invention, the spring tabs 16 of the surgical clip retainer 15 may have any shape suitable to provide downward force against a plurality of surgical clips 17. The upward tabs 22 of the surgical clip pusher 18 may have any shape suitable to provide upward force against a plurality of surgical clips 17.

The re-useable handle assembly 1 contains a distal opening 23 for receiving the proximal end 4 of the surgical cartridge assembly 2. Within the re-useable handle assembly 1, the proximal end of the flexure lock pusher 19 is attached a clip advancer 24. Furthermore, the proximal end of the cinch handle interface 14 is attached to a cinch advancer 25.

As illustrated in FIGS. 17-22, the re-useable handle assembly 1 has several trigger 26 positions. The re-useable handle assembly 1 and the surgical cartridge assembly 2, and all the elements contained therein, may operate at any rotation. Thus, the handle assembly 1 may be rotated to any angle to allow surgical clips 17 to be placed.

The movement of the trigger 26 from its initial starting position to a Step 1 position moves an internal first pivotable lever 29 and a cinch rod adaptor 28 in a distal direction. This moves the cinch advancer 25, the cinch 12, the cinch pusher 13, and the cinch handle interface 14 all in a distal direction. Jaw pins 27b on the right jaw 10 and 27a on the left jaw 11 move within the jaw leg guide 33 to wider the jaw legs 10 and 11. This opens the right jaw 10 and left jaw 11 to into a fully open position to receive the next surgical clip 17.

The movement of the trigger 26 from it's Step 1 position to a Step 2 position moves the first pivotable lever 29 in a distal direction and releases a ratchet mechanism 30. This ratchet 30 release moves a second pivotable lever 31 in a distal direction which moves the clip advancer 24, the clip pusher 18, and the flexure lock pusher 19 in a distal direction to load the next surgical clip into the fully open jaws 6. The ligating leg 20a of clip 17 moves into the curved indentation 32a of the left jaw 11. The ligating leg 20b of clip 17 moves into the curved indentation 32b of the right jaw 10.

The movement of the trigger 26 from it's Step 2 position to a Step 3 position moves the first pivotable lever 29, the cinch rod adaptor 28, the cinch advancer 25, the cinch 12, the cinch pusher 13, and the cinch handle interface 14 all in a distal direction. This begins advancement of the distal end of the cinch 12 over the jaw 6 to begin closing the jaws 6 to begin compressing the surgical clip 17. Jaw pins 27b on the right jaw 10 and 27a on the left jaw 11 move within the jaw leg guide 33 to narrow the position of the jaw legs 10 and 11. The jaws 6 increases the two equal compressive forces in opposing directions to the outer surface of each ligating leg 20a and 20b towards the center of the surgical clip 17. As jaws 6 increases the two equal compressive forces to the outer surface of each ligating leg 20a and 20b, the legs 20a and 20b bend at the apex connection 21 until the vessel diameter is reduced to a desired level. Apex connection 21 retains the closed position of the surgical clip 14 assuring that the vessel remains ligated.

The movement of the trigger 26 from it's Step 3 position to a Step 4 position moves the cinch advancer 25, the cinch 12, the cinch pusher 13, and the cinch handle interface 14 all in a distal direction to full ligation. Jaw pins 27b on the right jaw 10 and 27a on the left jaw 11 move within the jaw leg guide 33 to fully close the jaw legs 10 and 11 and fully ligate the surgical clip 17 within the jaws over the desired blood vessel by bending the ligating legs 20a and 20b at the apex connection 21.

The movement of the trigger 26 from it's Step 4 position to a Step 5 position moves the cinch advancer 25, the cinch 12, the cinch pusher 13, and the cinch handle interface 14 all in a distal direction to maximum stroke.

What is claimed is:

1. A surgical clip applier, comprising:
   a non-disposable housing re-useable between patients, the housing comprising a handle, and an opening on the housing;
   a drive mechanism movably disposed within the housing;
   a trigger attached to the housing, the trigger operably coupled to the drive mechanism, wherein application of compressive force to the trigger moves the trigger to from an initial, first position, to at least two subsequent consecutive positions relative to the housing, wherein each trigger position moves the drive mechanism from a first initial configuration to at least two subsequent consecutive configurations;
   a disposable and replaceable cartridge assembly removably coupled to the housing, the cartridge assembly comprising a tubular housing, a coupling assembly adapted to removably couple the cartridge assembly to the housing;
   a pair of surgical jaws on the distal end of the cartridge assembly, wherein each surgical jaw contains a protruding pin, and each surgical jaw contains a curved indentation for receiving and holding a leg of a surgical clip;
   a cinch rod disposed within the tubular housing, wherein the pins of the surgical jaws are contained within an indentation of the cinch rod, wherein the indentation comprises a jaw leg guide including a substantially triangular-shaped protrusion configured to control the spacing of the surgical jaws during actuation, wherein one vertex of the protrusion faces the handle and the protrusion expands in a distal direction to two other vertices facing a distal end of the clip applier;
   a linear array of sequentially centrally aligned surgical clips disposed within the tubular housing;
   a clip pusher disposed within the tubular housing;
   wherein prior to compression of the trigger, a space between the surgical clip jaws is not wide enough to receive a distal most surgical clip from the linear array of surgical clips;
   wherein compression of the trigger actuates the drive mechanism to move the cinch rod in a distal direction, moving the indentation of the cinch rod over the pins of the surgical jaws to a wider portion of the indentation, with the pins moving along the expanding sides of the triangular-shaped protrusion within the indentation, widening the space between the surgical clip jaws to permit reception of the distal most surgical clip from the linear array of surgical clips;

wherein continued compression of the trigger actuates the drive mechanism to move the clip pusher in a distal direction to load the distal most surgical clip from the linear array of clips into the open surgical clip jaws;

wherein continued compression of the trigger actuates the drive mechanism to move the cinch rod in a distal direction, moving the indentation of the cinch rod over the pins of the surgical jaws to a first narrow portion of the indentation wherein the two distal vertices of the protrusion curve inwardly, moving the pins inwardly and narrowing the space between the surgical clip jaws to begin closing the surgical clip jaws and compress the contained distal most surgical clip;

wherein continued compression of the trigger actuates the drive mechanism from the third configuration to a fourth configuration to move the cinch rod in a distal direction, moving the indentation of the cinch rod over the pins of the surgical jaws to a second narrow portion of the protrusion within the indentation, narrowing the space between the surgical clip jaws, to fully ligate the distal most surgical clip; and wherein the handle, drive mechanism, trigger, cartridge assembly, cinch rod, and linear array of surgical clips, and clip pusher may operate at any angle.

2. The surgical clip applier of claim 1, wherein the cartridge assembly is one of a 5 millimeter surgical clip cartridge or a 10 millimeter surgical clip cartridge.

3. The surgical clip applier of claim 1, wherein each surgical clip comprises a pair of opposed elongated ligating legs that have substantially uniform widths and lengths.

4. The surgical clip applier of claim 1, wherein the trigger is configured to be moved from a first initial position to a second, a third, a fourth, a fifth, and a sixth position relative to the housing to move the drive mechanism from a first initial configuration to a second, a third, a fourth, a fifth, and a sixth configuration.

5. The surgical clip applier of claim 1, wherein the surgical clip jaws compress the contained distal most surgical clip by applying two substantially equal compressive forces in opposing directions to the outer surface of ligating legs towards the center of the surgical clip, such that the ligating legs bend at an apex connection until a vessel diameter is reduced to a desired level.

6. An endoscopic surgical clip applier, comprising:
a non-disposable housing re-useable between patients, the housing comprising a handle attached to a bottom surface of the housing, and an opening on a distal end of the housing;
a drive mechanism movably disposed within the housing;
a trigger attached to the bottom surface of the housing, the trigger operably coupled to the drive mechanism, wherein application of compressive force to the trigger moves the trigger in a proximal direction, wherein the trigger is configured to be moved from a first initial position to multiple consecutive positions relative to the housing, wherein each trigger position moves the drive mechanism from a first initial configuration to multiple separate consecutive configurations;
an elongated disposable and replaceable cartridge assembly removably coupled to the housing and extending along a shaft axis from a proximal end to a distal end, the cartridge assembly comprising a hollow tubular housing, a coupling assembly disposed on the proximal end of the tubular housing and adapted to removably couple the proximal end of the cartridge assembly to the re-useable housing;
a pair of surgical jaws on the distal end of the cartridge assembly, wherein each surgical jaw contains a protruding pin, and each surgical jaw contains a curved indentation for receiving and holding a leg of a surgical clip;
a cinch rod disposed within the tubular housing, wherein the pins of the surgical jaws are contained within an indentation of the cinch rod, wherein the indentation comprises a jaw leg guide including a substantially triangular-shaped protrusion configured to control the spacing of the surgical jaws during actuation, wherein one vertex of the protrusion faces the handle and the protrusion expands in a distal direction to two other vertices facing a distal end of the clip applier, wherein the cinch rod extends along the shaft axis;
a substantially flat insert disposed beneath the cinch rod, within the tubular housing, wherein the flat insert extends along the shaft axis, wherein the flat insert further comprises a plurality of sequentially centrally aligned protrusions that extend in a downward direction;
a linear array of sequentially centrally aligned surgical clips disposed within the tubular housing beneath the plurality of sequentially centrally aligned protrusions, wherein the linear array extends along the shaft axis;
a substantially flat clip pusher disposed beneath the linear array of surgical clips within the tubular housing, wherein the clip pusher extends along the shaft axis, wherein the top surface of the clip pusher comprises a second plurality of protrusions disposed beneath the linear array of surgical clips;
wherein prior to compression of the trigger, a space between the surgical clip jaws is not wide enough to receive a distal most surgical clip from the linear array of surgical clips;
wherein compression of the trigger in a proximal direction from an initial position to a second position actuates the drive mechanism from a initial configuration to a second configuration to move the cinch rod in a distal direction, moving the indentation of the cinch rod over the pins of the surgical jaws to a wider portion of the indentation, with the pins moving along the expanding sides of the triangular-shaped protrusion within the indentation, widening the space between the surgical clip jaws to permit reception of the distal most surgical clip from the linear array of surgical clips;
wherein continued compression of the trigger in a proximal direction from the second position to a third position actuates the drive mechanism from the second configuration to a third configuration to move the clip pusher in a distal direction to load the distal most surgical clip from the linear array of clips into the open surgical clip jaws;
wherein continued compression of the trigger in a proximal direction from the third position to a fourth position actuates the drive mechanism from the third configuration to a fourth configuration to move the cinch rod in a distal direction, moving the indentation of the cinch rod over the pins of the surgical jaws to a first narrow portion of the indentation, wherein the two distal vertices of the protrusion curve inwardly, moving the pins inwardly and narrowing the space between the surgical clip jaws to begin closing the surgical clip jaws and compress the contained distal most surgical clip;

wherein continued compression of the trigger in a proximal direction from the fourth position to a fifth position actuates the drive mechanism from the third configuration to a fourth configuration to move the cinch rod in a distal direction, moving the indentation of the cinch rod over the pins of the surgical jaws to a second narrow portion of the protrusion within the indentation, narrowing the space between the surgical clip jaws, to fully ligate the distal most surgical clip; and wherein the handle, drive mechanism, trigger, cartridge assembly, cinch rod, and linear array of surgical clips, and clip pusher may operate at any angle.

7. An endoscopic surgical clip applier, comprising:

a non-disposable housing re-useable between patients, the housing comprising a handle, and an opening on a distal end of the housing;

a drive mechanism movably disposed within the housing;

a trigger attached to the housing, the trigger operably coupled to the drive mechanism, wherein application of compressive force to the trigger moves the trigger in a proximal direction from a first initial position to subsequent consecutive positions relative to the housing, wherein each trigger position moves the drive mechanism from a first initial configuration to subsequent configurations;

a disposable and replaceable cartridge assembly removably coupled to the housing and extending along a shaft axis from a proximal end to a distal end, the cartridge assembly comprising a hollow tubular housing, a coupling assembly disposed on the proximal end of the tubular housing and adapted to removably couple the proximal end of the cartridge assembly to the re-useable housing;

a pair of surgical jaws on the distal end of the cartridge assembly, wherein each surgical jaw contains a protruding pin, and each surgical jaw contains a curved indentation for receiving and holding a leg of a surgical clip;

a cinch rod disposed within the tubular housing, wherein the pins of the surgical jaws are contained within an indentation of the cinch rod, wherein the indentation comprises a jaw leg guide including a substantially triangular-shaped protrusion configured to control the spacing of the surgical jaws during actuation, wherein one vertex of the protrusion faces the handle and the protrusion expands in a distal direction to two other vertices facing a distal end of the clip applier, wherein the cinch rod extends along the shaft axis;

an insert disposed beneath the cinch rod, within the tubular housing, wherein the insert extends along the shaft axis, wherein the insert further comprises a plurality of sequentially centrally aligned protrusions that extend in a downward direction;

a linear array of sequentially centrally aligned surgical clips disposed within the tubular housing beneath the plurality of sequentially centrally aligned protrusions, wherein the linear array extends along the shaft axis;

a clip pusher disposed beneath the linear array of surgical clips within the tubular housing, wherein the clip pusher extends along the shaft axis, wherein the top surface of the clip pusher comprises a second plurality of protrusions disposed beneath the linear array of surgical clips;

wherein prior to compression of the trigger, a space between the surgical clip jaws is not wide enough to receive a distal most surgical clip from the linear array of surgical clips;

wherein compression of the trigger in a proximal direction from an initial position to a second position actuates the drive mechanism from a initial configuration to a second configuration to move the cinch rod in a distal direction, moving the indentation of the cinch rod over the pins of the surgical jaws to a wider portion of the indentation, with the pins moving along the expanding sides of the triangular-shaped protrusion within the indentation, widening the space between the surgical clip jaws to permit reception of the distal most surgical clip from the linear array of surgical clips;

wherein continued compression of the trigger in a proximal direction from the second position to a third position actuates the drive mechanism from the second configuration to a third configuration to move the clip pusher in a distal direction to load the distal most surgical clip from the linear array of clips into the open surgical clip jaws;

wherein continued compression of the trigger in a proximal direction from the third position to a fourth position actuates the drive mechanism from the third configuration to a fourth configuration to move the cinch rod in a distal direction, moving the indentation of the cinch rod over the pins of the surgical jaws to a first narrow portion of the indentation, wherein the two distal vertices of the protrusion curve inwardly, moving the pins inwardly and narrowing the space between the surgical clip jaws to begin closing the surgical clip jaws and compress the contained distal most surgical clip;

wherein continued compression of the trigger in a proximal direction from the fourth position to a fifth position actuates the drive mechanism from the third configuration to a fourth configuration to move the cinch rod in a distal direction, moving the indentation of the cinch rod over the pins of the surgical jaws to a second narrow portion of the protrusion within the indentation, narrowing the space between the surgical clip jaws, to fully ligate the distal most surgical clip; and wherein the handle, drive mechanism, trigger, cartridge assembly, cinch rod, and linear array of surgical clips, and clip pusher may operate at any angle.

8. The endoscopic surgical clip applier of claim 7, wherein the cartridge assembly is one of a 5 millimeter surgical clip cartridge or a 10 millimeter surgical clip cartridge.

9. The endoscopic surgical clip applier of claim 7, wherein each surgical clip comprises a pair of opposed elongated ligating legs that have substantially uniform widths and lengths.

10. The endoscopic surgical clip applier of claim 7, wherein the trigger is configured to be moved from a first initial position to a second, a third, a fourth, a fifth, and a sixth position relative to the housing to move the drive mechanism from a first initial configuration to a second, a third, a fourth, a fifth, and a sixth configuration.

11. The endoscopic surgical clip applier of claim 7, wherein the surgical clip jaws compress the contained distal most surgical clip by applying two substantially equal compressive forces in opposing directions to the outer surface of ligating legs towards the center of the surgical clip, such that the ligating legs bend at an apex connection until a vessel diameter is reduced to a desired level.

* * * * *